(12) United States Patent
Clark et al.

(10) Patent No.: US 12,285,482 B2
(45) Date of Patent: *Apr. 29, 2025

(54) THERAPEUTIC VACCINE FOR HEPATITIS B VIRUS (HBV) USING THE HBV PreS1 AND/OR PreS2, AND/OR S-HBsAg REGIONS OF THE HBV ENVELOPE PROTEIN

(71) Applicants: University of Washington, Seattle, WA (US); ABACUS BIOSCIENCE, INC., Sammamish, WA (US)

(72) Inventors: Edward A. Clark, Seattle, WA (US); Che-Leung Law, Seattle, WA (US); Deborah Fuller, Seattle, WA (US); Michael Gale, Seattle, WA (US)

(73) Assignees: UNIVERSITY OF WASHINGTON, Seattle, WA (US); ABACUS BIOSCIENCE, INC., Sammamish, WA (US)

( * ) Notice: Subject to any disclaimer, the term of this patent is extended or adjusted under 35 U.S.C. 154(b) by 88 days.

This patent is subject to a terminal disclaimer.

(21) Appl. No.: 17/810,480

(22) Filed: Jul. 1, 2022

(65) Prior Publication Data

US 2023/0053634 A1 Feb. 23, 2023

Related U.S. Application Data

(63) Continuation of application No. 16/764,950, filed as application No. PCT/US2018/061218 on Nov. 15, 2018, now Pat. No. 11,389,532.

(60) Provisional application No. 62/587,051, filed on Nov. 16, 2017.

(51) Int. Cl.
| | |
|---|---|
| *A61K 39/29* | (2006.01) |
| *A61K 39/00* | (2006.01) |
| *A61P 31/20* | (2006.01) |
| *C07K 16/28* | (2006.01) |

(52) U.S. Cl.
CPC ............ *A61K 39/292* (2013.01); *A61P 31/20* (2018.01); *C07K 16/2878* (2013.01); *C07K 16/2896* (2013.01); *A61K 2039/6056* (2013.01); *C07K 2317/524* (2013.01); *C07K 2317/526* (2013.01); *C07K 2317/56* (2013.01); *C07K 2317/622* (2013.01)

(58) Field of Classification Search
None
See application file for complete search history.

(56) References Cited

U.S. PATENT DOCUMENTS

| | | |
|---|---|---|
| 10,196,614 B2 | 2/2019 | Clark et al. |
| 10,563,179 B2 | 2/2020 | Clark et al. |
| 11,389,532 B2 * | 7/2022 | Clark ............... A61K 39/12 |
| 2012/0020965 A1 | 1/2012 | Chaplin et al. |
| 2013/0017200 A1 | 1/2013 | Scheer et al. |
| 2013/0209395 A1 | 8/2013 | Weiner et al. |
| 2017/0260258 A1 | 9/2017 | Hong et al. |

FOREIGN PATENT DOCUMENTS

| | | |
|---|---|---|
| WO | 1997/04000 | 2/1997 |
| WO | 2009/036228 | 3/2009 |
| WO | 2017/176319 | 10/2017 |
| WO | 2017176319 A1 | 10/2017 |

OTHER PUBLICATIONS

Alving et al. (2012) Adjuvants for human vaccines. Curr Opin Immunol. 24:310-5.
Beck et al. (2007) Hepatitis 8 virus replication. World J Gastroenterol WJG. 13:48-64.
Bertoletti et al. (2016) Adaptive immunity in H8V infection. J Hepatol. 64:S71-83.
Bian et al. (2017) Vaccines Targeting PreS1 Domain Overcome Immune Tolerance in HBV Carrier Mice. Hepatology. Apr. 26. doi:1002/hep.29239.
Bruss V. (2007) Hepatitis B virus morphogenesis. World J Gastroenterol. 13:65-73.
Chaplin et al. (2013) Targeting antigens to CD180 rapidly induces antigen-specific IgG, affinity maturation and immunologic memory. J Exp Med. 210:2135-46.
Chaplin et al. (2011) Anti-CD180 (RP105) activates B cells to rapidly produce polyclonal Ig via aT cell and My088-independent pathway. J Immunol. 187:4199-209.
Chappell et al. (2014) Controlling immune responses by targeting antigensto dendritic cell subsets and B Cells. Int Immunol. 26:3-11.
Chen et al. (2016) Selection of affinity-improved neutralizing human scFv against HBV PreS1 from CDR3 VHNL mutant library. Biologicals. July;44(4):271-5.
Chi et al. (2009) Broadly neutralizing anti-HBV antibody binds to non-epitope regions of preS1. FEBS Lett. 583:3095-100.
Clark et al. (1989) Activation of human B cells. Comparison of the signal transduced by IL-4 to four different competence signals. J Immunol. 143:3873-80.
Coffman et al. (2010) Vaccine adjuvants: putting innate immunity to work. Immunity. 33:492-503.
Dion et al. (2013) Adena-associated virus-mediated gene transfer leads to persistent hepatitis B virus replication in mice expressing HLA-A2 and HLA-DR1 molecules. J Virol. May;87(10):5554-63.
Eng et al. (2013) The potential of 1018 ISS adjuvant in hepatitis 8 vaccines: HEPLISAV™. Hum Vaccin Immunother. 9:1661-72.
Ferrari et al. (1989) The preS1 antigen of hepatitis B virus is highly immunogenic at the T cell level in man. J Clin Invest. 84:1314-9.
Gerlich WH. (2015) Prophylactic vaccination against hepatitis 8: achievements, challenges and perspectives. Med BiolImmunol. 204:39-55.

(Continued)

*Primary Examiner* — Phuong Huynh
(74) *Attorney, Agent, or Firm* — McDonnell Boehnen Hubert & Berghoff, LLC

(57) ABSTRACT

Compositions including a CD180 binding ligand and a linked Hepatitis B antigen and their use are disclosed. The Hepatitis B antigen includes Hepatitis B virus pre-S1 and/or pre-S2 region of the HBV envelope protein (HBVpreS1/S2Ag), L-HBsAg, MHBsAg, S-HBsAg, or antigenic fragments or mutants thereof.

20 Claims, 6 Drawing Sheets

Specification includes a Sequence Listing.

(56) References Cited

OTHER PUBLICATIONS

Hebeis et al. (2005) Vav proteins are required forB-lymphocyte responses to LPS. Blood. 106:63540.

Hebeis et al. (2004)Activation of virus-specific memory B cells in the absence of T cell help. J Exp Med. 199:593-602.

Hepatitis 8 Vaccines (2004) Releve epidemiologique hebdomadaire I Section d'hygiene du Secretariat de la Societe des Nations = Weekly epidemiological record I Health Section of the Secretariat of the League of Nations. 79:255-63.

Jilg W. (1998) Novel hepatitis 8 vaccines. Vaccine. 16 Suppi:S65-8.

Kim et al. (2009) Hepatitis 8 vaccination in HIV-infected adults: current evidence, recommendations and practical considerations. International journal of STD & AIDS.

Kim WR. (2009) Epidemiology of hepatitis B in the United States. Hepatology. 49:S28-34.

Krawczyk et al. (2014) Induction of a robust T- and B-cell immune response in non- and low-responders to conventional vaccination against hepatitis B by using a third generation PreS/S vaccine. Vaccine. 32:5077-82.

Kubba (2003) et al. Non-responders to hepatitis 8 vaccination: a review. Communicable disease and public health PHLS. 106-12.

Lavanchy D. (2004) Hepatitis 8 virus epidemiology, disease burden, treatment, and current and emerging prevention and control measures. J. Viral Hep. 11:97-107.

Li W. (2015) NTCP is receptor for HBV The hepatitis 8 virus receptor. Annu Rev Cell Dev Bioi. 31:125-47.

Liang al. (2011) Predictors of relapse in chronic hepatitis B after discontinuation of anti-viral therapy. Aliment Pharmacal Ther. 34:344-52.

Loudon et al. (2010) GM-CSF increases mucosal and PA, GM-CSF increases mucosal and systemic immunogenicity fo an H1N1 influenza DNA vaccine administered into the epidermis of non-human primates. PLoS One. 5:e11021.

Luckhaupt et al. (2008) Deaths due to bloodborne infections and their sequelae among health-care workers. Am J Ind Med. 51:812-24.

Madalinski et al. (2001) Antibody responses to preS components after immunization of children with low doses of BioHepB. Vaccine. Oct. 12, 2020(1-2):92-7.

Maxon et al. (2011) The next decade of vaccines: societal and scientific challenges. Lancet. 378:348-59.

Menendez-Aria et al. (2014) Nucleoside/nucleotide analog inhibitors of hepatitis 8 virus polymerase: mechanism of action and resistance. Curr Opin Viral. 8C:1-9.

Mitchell et al. (2011) The increasing burden of imported chronic hepatitis 8—United States, 1974-2008. PLoS One. 6:e27717.

Miyake et al. (1994) Murine B cell proliferation and protection from apoptosis with an antibody against a 105-kD molecule: unresponsiveness of X-linked immunodeficient B cells. J Exp Med. 180:1217-24.

Miyake et al. (1995) RP105, a novel B cell surface molecule implicated in B cell activation, is a member of the leucine-rich repeat protein family. J Immunol. 154:3333-40.

Ni et al. (2014) Hepatitis 8 and D viruses exploit sodium taurocholate co-transporting polypeptide for species-specific entry into hepatocytes. Gastroenterology. Apr 146(4):1070-83.

Ohto et al. (2011) Crystal structures of mouse and human RP105/MD-1complexes reveal unique dimer organization of the toll-like receptor family. J Mol Bioi. Nov. 4:413(4):815-25.

Ott et al. (2012) Global epidemiology of hepatitis 8 virus infection: new estimates of age-specific H8cAG seroprevalence and endemicity. Vaccine. 30:2212-9.

Perz et al. (2006) The contributions of hepatitis 8 virus and hepatitis C virus infections to cirrhosis and primary liver cancer worldwide. J Hepatol. 45:529-38.

Ramos H.J. (2011) RIG-I like receptors and their signaling crosstalk in the regulation of antiviral immunity. Curr Opin Virol.1:67-76.

Rendi-Wagner et al. (2006) Comparative immunogenicity of a PreS/S hepatitis 8 vaccine in non and low responders to conventional vaccine. Vaccine. 24:2871-9.

Schultz et al. (2017) The RP105/MD-1 complex: molecular signaling mechanisms and pathophysiological implications. J Leukoc Bioi. Jan:101(1):183-192.

Shimazu et al. (1999) MD-2, a molecule that confers lipopolysaccharide responsiveness on Toll-like receptor4. J Exp. Med. 189:1777-82.

Suthar et al. (2013) West Nile virus infection and immunity. Nat. Rev Microbiol. 11:115-128.

Thai et al. (2012) Convergence and coevolution of hepatitis 8 virus drug resistance. Nat Commun. 3:789.

Toita et al. (2015) Applications of human hepatitis B virus preS domain in bio- and nanotechnology. World J Gastroenterol. Jun. 28:21(24):7400-11.

Valatine et al. (1988) Antibody to a novel 95-kDa surface glycoprotein on human B cells induces calcium mobilization and B cell activation. J Immunol. 140:4071-8.

Wang et al. (2014) Immunotherapeutic interventions in chronic hepatitis 8 virus infection: a review. J Immunol Methods. May:407:1-8.

Wasley et al. (2010) The prevalence of hepatitis 8 virus infection in the United States in the era of vaccination. J Infect Dis. 202:192-201.

Weinbaum CM, (2008) Recommendations for identification and public health management of persons with chronic hepatitis 8 virus infection. Centers for Disease Control and Prevention (CDC). MMWR Recomm. Rep 57(RR-8):1-20.

Wiegand et al. (2010) Management of chronic hepatitis 8: status and challenges beyond treatment guidelines. Semin Liver Dis. 30:361-377.

Yazawa et al., (2003) CD19 regulates innate immunity by the toll-like receptor RP105 signaling in B lymphocytes. Blood. 102:1374-80.

Yoon et al. (2011) An unusual dimeric structure and assembly for TLR4 regulator RP105-MD-1. Nat Struct Mol Bioi. 2. Aug. 21:18(9):1028-35.

The International Search Report (ISR) with Written Opinion for PCT/US2018/061218 dated Feb. 5, 2019, pp. 1-11.

LLoyd et al. Protein Engineering, Design & Selection 22: 159-168 (Year: 2009).

Edwards et al., J Mol Biol. 334(1 ): 103-118 (Year: 2003).

Rudikoff et al., Proc. Natl. Acad. Sci. USA, 79:1979-1983 (Year: 1982).

\* cited by examiner

A

B

SEQUENCE LISTING

```
Sequence total quantity: 69
SEQ ID NO: 1           moltype = AA  length = 174
FEATURE                Location/Qualifiers
REGION                 1..174
                       note = Synthetic peptide
source                 1..174
                       mol_type = protein
```

```
                            organism = synthetic construct
SEQUENCE: 1
MGGWSSKPRQ GMGTNLSVPN PLGFFPDHQL DPAFGANSNN PDWDFNPNKD HWPEANQVGA    60
GAFGPGFTPP HGGLLGWSPQ AQGILTTLPA APPPASTNRQ SGRQPTPISP PLRDSHPQAM   120
QWNSTTFHQA LLDPRVRGLY FPAGGSSSGT VNPVPTTASP ISSIFSRTGD PAPN         174

SEQ ID NO: 2            moltype = AA  length = 108
FEATURE                 Location/Qualifiers
REGION                  1..108
                        note = Synthetic peptide
source                  1..108
                        mol_type = protein
                        organism = synthetic construct
SEQUENCE: 2
MGGWSSKPRQ GMGTNLSVPN PLGFFPDHQL DPAFGANSNN PDWDFNPNKD HWPEANQVGA    60
GAFGPGFTPP HGGLLGWSPQ AQGILTTLPA APPPASTNRQ SGRQPTPI               108

SEQ ID NO: 3            moltype = AA  length = 66
FEATURE                 Location/Qualifiers
REGION                  1..66
                        note = Synthetic peptide
source                  1..66
                        mol_type = protein
                        organism = synthetic construct
SEQUENCE: 3
SPPLRDSHPQ AMQWNSTTFH QALLDPRVRG LYFPAGGSSS GTVNPVPTTA SPISSIFSRT    60
GDPAPN                                                               66

SEQ ID NO: 4            moltype = AA  length = 400
FEATURE                 Location/Qualifiers
REGION                  1..400
                        note = Synthetic peptide
source                  1..400
                        mol_type = protein
                        organism = synthetic construct
SEQUENCE: 4
MGGWSSKPRQ GMGTNLSVPN PLGFFPDHQL DPAFGANSNN PDWDFNPNKD HWPEANQVGA    60
GAFGPGFTPP HGGLLGWSPQ AQGILTTLPA APPPASTNRQ SGRQPTPISP PLRDSHPQAM   120
QWNSTTFHQA LLDPRVRGLY FPAGGSSSGT VNPVPTTASP ISSIFSRTGD PAPNMESTTS   180
GFLGPLLVLQ AGFFLLTRIL TIPQSLDSWW TSLNFLGGAP TCPGQNSQSP TSNHSPTSCP   240
PTCPGYRWMC LRRFIIFLFI LLLCLIFLLV LLDYQGMLPV CPLLPGTSTT STGPCRTCTI   300
PAQGTSMFPS CCCTKPSDGN CTCIPIPSSW AFARFLWEWA SVRFSWLSLL VPFVQWFVGL   360
SPTVWLSAIW MMWYWGPSLY NILSPFLPLL PIFFCLWVYI                         400

SEQ ID NO: 5            moltype = AA  length = 291
FEATURE                 Location/Qualifiers
REGION                  1..291
                        note = Synthetic peptide
source                  1..291
                        mol_type = protein
                        organism = synthetic construct
SEQUENCE: 5
PPLRDSHPQA MQWNSTTFHQ ALLDPRVRGL YFPAGGSSSG TVNPVPTTAS PISSIFSRTG    60
DPAPNMESTT SGFLGPLLVL QAGFFLLTRI LTIPQSLDSW WTSLNFLGGA PTCPGQNSQS   120
PTSNHSPTSC PPTCPGYRWM CLRRFIIFLF ILLLCLIFLL VLLDYQGMLP VCPLLPGTST   180
TSTGPCRTCT IPAQGTSMFP SCCCTKPSDG NCTCIPIPSS WAFARFLWEW ASVRFSWLSL   240
LVPFVQWFVG LSPTVWLSAI WMMWYWGPSL YNILSPFLPL LPIFFCLWVY I            291

SEQ ID NO: 6            moltype = AA  length = 226
FEATURE                 Location/Qualifiers
REGION                  1..226
                        note = Synthetic peptide
source                  1..226
                        mol_type = protein
                        organism = synthetic construct
SEQUENCE: 6
MESTTSGFLG PLLVLQAGFF LLTRILTIPQ SLDSWWTSLN FLGGAPTCPG QNSQSPTSNH    60
SPTSCPPTCP GYRWMCLRRF IIFLFILLLC LIFLLVLLDY QGMLPVCPLL PGTSTTSTGP   120
CRTCTIPAQG TSMFPSCCCT KPSDGNCTCI PIPSSWAFAR FLWEWASVRF SWLSLLVPFV   180
QWFVGLSPTV WLSAIWMMWY WGPSLYNILS PFLPLLPIFF CLWVYI                  226

SEQ ID NO: 7            moltype = AA  length = 108
FEATURE                 Location/Qualifiers
REGION                  1..108
                        note = Synthetic peptide
source                  1..108
                        mol_type = protein
                        organism = synthetic construct
SEQUENCE: 7
```

```
MGGWSAKPRK GMGTNLSVPN PLGFFPDHQL DPAFGANSNN PDWDFNPNKD HWPEANQVGV     60
GAFGPGFTPP HGGLLGWSSQ AQGTLHTVPA VPPPASTNRQ TGRQPTPI                108

SEQ ID NO: 8              moltype = AA  length = 55
FEATURE                   Location/Qualifiers
REGION                    1..55
                          note = Synthetic peptide
source                    1..55
                          mol_type = protein
                          organism = synthetic construct
SEQUENCE: 8
SPPLRDSHPQ AMQWNSTAFQ QALQDPRVRG LFFPAGGSSS GTVNPAPNIA SHISS          55

SEQ ID NO: 9              moltype = AA  length = 236
FEATURE                   Location/Qualifiers
REGION                    1..236
                          note = Synthetic peptide
source                    1..236
                          mol_type = protein
                          organism = synthetic construct
SEQUENCE: 9
ISSRTGDPAL NMENITSGFL GPLLVLQAGF FLLTRILTIP QSLDSWWTSL NFLGGSPVCL     60
GQNSQSPTSN HSPTSCPPIC PGYRWMCLRR FIIFLFILLL CLIFLLVLLD YQGMLPVCPL    120
IPGSTTTSTG PCKTCTTPAQ GNSMFPCCCT KPTDGNCTCI PIPSSWAFAK YLWEWASVRF    180
SWLSLLVPFV QWFVGLSPTV WLSVIWMMWY WGPSLYNILS PFIPLLPIFF CLWVYI        236

SEQ ID NO: 10             moltype = AA  length = 291
FEATURE                   Location/Qualifiers
REGION                    1..291
                          note = Synthetic peptide
source                    1..291
                          mol_type = protein
                          organism = synthetic construct
SEQUENCE: 10
SPPLRDSHPQ AMQWNSTAFQ QALQDPRVRG LFFPAGGSSS GTVNPAPNIA SHISSISSRT     60
GDPALNMENI TSGFLGPLLV LQAGFFLLTR ILTIPQSLDS WWTSLNFLGG SPVCLGQNSQ    120
SPTSNHSPTS CPPICPGYRW MCLRRFIIFL FILLLCLIFL LVLLDYQGML PVCPLIPGST    180
TTSTGPCKTC TTPAQGNSMF PCCCTKPTDG NCTCIPIPSS WAFAKYLWEW ASVRFSWLSL    240
LVPFVQWFVG LSPTVWLSVI WMMWYWGPSL YNILSPFIPL LPIFFCLWVY I             291

SEQ ID NO: 11             moltype = AA  length = 400
FEATURE                   Location/Qualifiers
REGION                    1..400
                          note = Synthetic peptide
source                    1..400
                          mol_type = protein
                          organism = synthetic construct
SEQUENCE: 11
MGGWSAKPRK GMGTNLSVPN PLGFFPDHQL DPAFGANSNN PDWDFNPNKD HWPEANQVGV     60
GAFGPGFTPP HGGLLGWSSQ AQGTLHTVPA VPPPASTNRQ TGRQPTPISP PLRDSHPQAM    120
QWNSTAFQQA LQDPRVRGLF FPAGGSSSGT VNPAPNIASH ISSISSRTGD PALNMENITS    180
GFLGPLLVLQ AGFFLLTRIL TIPQSLDSWW TSLNFLGGSP VCLGQNSQSP TSNHSPTSCP    240
PICPGYRWMC LRRFIIFLFI LLLCLIFLLV LLDYQGMLPV CPLIPGSTTT STGPCKTCTT    300
PAQGNSMFPS CCCTKPTDGN CTCIPIPSSW AFAKYLWEWA SVRFSWLSLL VPFVQWFVGL    360
SPTVWLSVIW MMWYWGPSLY NILSPFIPLL PIFFCLWVYI                          400

SEQ ID NO: 12             moltype = AA  length = 108
FEATURE                   Location/Qualifiers
REGION                    1..108
                          note = Synthetic peptide
source                    1..108
                          mol_type = protein
                          organism = synthetic construct
SEQUENCE: 12
MGGWSSKPRK GMGTNLSVPN PLGFFPDHQL DPAFGANSNN PDWDFNPVKD DWPAANQVGV     60
GAFGPRLTPP HGGILGWSPQ AQGILTTVST IPPPASTNRQ SGRQPTPI                 108

SEQ ID NO: 13             moltype = AA  length = 55
FEATURE                   Location/Qualifiers
REGION                    1..55
                          note = Synthetic peptide
source                    1..55
                          mol_type = protein
                          organism = synthetic construct
SEQUENCE: 13
SPPLRDSHPQ AMQWNSTAFH QTLQDPRVRG LYLPAGGSSS GTVNPAPNIA SHISS          55

SEQ ID NO: 14             moltype = AA  length = 237
FEATURE                   Location/Qualifiers
```

```
REGION                          1..237
                                note = Synthetic peptide
source                          1..237
                                mol_type = protein
                                organism = synthetic construct
SEQUENCE: 14
ISARTGDPVT NMENITSGFL GPLLVLQAGF FLLTRILTIP QSLDSWWTSL NFLGGSPVCL    60
GQNSQSPTSN HSPTSCPPIC PGYRWMCLRR FIIFLFILLL CLIFLLVLLD YQGMLPVCPL   120
IPGSTTTSTG PCKTCTTPAQ GNSMFPSCCC TKPTDGNCTC IPIPSSWAFA KYLWEWASVR   180
FSWLSLLVPF VQWFVGLSPT VWLSAIWMMW YWGPSLYSIV SPFIPLLPIF FCLWVYI      237

SEQ ID NO: 15                   moltype = AA  length = 292
FEATURE                         Location/Qualifiers
REGION                          1..292
                                note = Synthetic peptide
source                          1..292
                                mol_type = protein
                                organism = synthetic construct
SEQUENCE: 15
SPPLRDSHPQ AMQWNSTAFH QTLQDPRVRG LYLPAGGSSS GTVNPAPNIA SHISSISART    60
GDPVTNMENI TSGFLGPLLV LQAGFFLLTR ILTIPQSLDS WWTSLNFLGG SPVCLGQNSQ   120
SPTSNHSPTS CPPICPGYRW MCLRRFIIFL FILLLCLIPFL LVLLDYQGML PVCPLIPGST   180
TTSTGPCKTC TTPAQGNSMF PSCCCTKPTD GNCTCIPIPS SWAFAKYLWE WASVRFSWLS   240
LLVPFVQWFV GLSPTVWLSA IWMMWYWGPS LYSIVSPFIP LLPIFFCLWV YI           292

SEQ ID NO: 16                   moltype = AA  length = 400
FEATURE                         Location/Qualifiers
REGION                          1..400
                                note = Synthetic peptide
source                          1..400
                                mol_type = protein
                                organism = synthetic construct
SEQUENCE: 16
MGGWSSKPRK GMGTNLSVPN PLGFFPDHQL DPAFGANSNN PDWDFNPVKD DWPAANQVGV    60
GAFGPRLTPP HGGILGWSPQ AQGILTTVST IPPPASTNRQ SGRQPTPISP PLRDSHPQAM   120
QWNSTAFHQT LQDPRVRGLY LPAGGSSSGT VNPAPNIASH ISSISARTGD PVTNMENITS   180
GFLGPLLVLQ AGFFLLTRIL TIPQSLDSWW TSLNFLGGSP VCLGQNSQSP TSNHSPTSCP   240
PICPGYRWMC LRRFIIFLFI LLLCLIFLLV LLDYQGMLPV CPLIPGSTTT STGPCKTCTT   300
PAQGNSMFPS CCCTKPTDGN CTCIPIPSSW AFAKYLWEWA SVRFSWLSLL VPFVQWFVGL   360
SPTVWLSAIW MMWYWGPSLY SIVSPFIPLL PIFFCLWVYI                         400

SEQ ID NO: 17                   moltype = AA  length = 108
FEATURE                         Location/Qualifiers
REGION                          1..108
                                note = Synthetic peptide
source                          1..108
                                mol_type = protein
                                organism = synthetic construct
SEQUENCE: 17
MGGRLPKPRK GMGTNLSVPN PLGFFPDHQL DPAFGANSNN PDWDFNPIKD HWPQANQVGV    60
GAFGPGFTPP HGGVLGWSPQ AQGTLTTVPA VPPPASTNRQ SGRQPTPI                108

SEQ ID NO: 18                   moltype = AA  length = 55
FEATURE                         Location/Qualifiers
REGION                          1..55
                                note = Synthetic peptide
source                          1..55
                                mol_type = protein
                                organism = synthetic construct
SEQUENCE: 18
SPPLRDSHPQ AMQWNSTKFH QTLQDPRVRG LYFPAGGSSS GTVNPAPNIA SHISS          55

SEQ ID NO: 19                   moltype = AA  length = 237
FEATURE                         Location/Qualifiers
REGION                          1..237
                                note = Synthetic peptide
source                          1..237
                                mol_type = protein
                                organism = synthetic construct
SEQUENCE: 19
ISSRIGDPAP TMENITSGFL GPLLVLQAGF FLLTRILTIP QSLDSWWTSL NFLGEAPVCL    60
GQNSQSPTSN HSPTSCPPIC PGYRWMCLRR FIIFLFILLL CLIFLLVLLD CQGMLPVCPL   120
IPGSTTTSTG PCRTCTTPAQ GNSMFPSCCC TKPTDGNCTC IPIPSSWAFA KYLWEWASVR   180
FSWLSLLVPF VQWFVGLSPT VWLSVIWMMW YWGPSLYNIL SPFIPLLPIF FCLWVYI      237

SEQ ID NO: 20                   moltype = AA  length = 292
FEATURE                         Location/Qualifiers
REGION                          1..292
                                note = Synthetic peptide
```

```
                        source          1..292
                                        mol_type = protein
                                        organism = synthetic construct
SEQUENCE: 20
SPPLRDSHPQ AMQWNSTKFH QTLQDPRVRG LYFPAGGSSS GTVNPAPNIA SHISSISSRI    60
GDPAPTMENI TSGFLGPLLV LQAGFFLLTR ILTIPQSLDS WWTSLNFLGE APVCLGQNSQ   120
SPTSNHSPTS CPPICPGYRW MCLRRFIIFL FILLLCLIFL LVLLDCQGML PVCPLIPGST   180
TTSTGPCRTC TTPAQGNSMF PSCCCTKPTD GNCTCIPIPS SWAFAKYLWE WASVRFSWLS   240
LLVPFVQWFV GLSPTVWLSV IWMMYWGPS LYNILSPFIP LLPIFFCLWV YI            292

SEQ ID NO: 21           moltype = AA   length = 400
FEATURE                 Location/Qualifiers
REGION                  1..400
                        note = Synthetic peptide
source                  1..400
                        mol_type = protein
                        organism = synthetic construct
SEQUENCE: 21
MGGRLPKPRK GMGTNLSVPN PLGFFPDHQL DPAFGANSNN PDWDFNPIKD HWPQANQVGV    60
GAFGPGFTPP HGGVLGWSPQ AQGTLTTVPA VPPPASTNRQ SGRQPTPISP PLRDSHPQAM   120
QWNSTKFHQT LQDPRVRGLY FPAGGSSSGT VNPAPNIASH ISSISSRIGD PAPTMENITS   180
GFLGPLLVLQ AGFFLLTRIL TIPQSLDSWW TSLNFLGEAP VCLGQNSQSP TSNHSPTSCP   240
PICPGYRWMC LRRFIIFLFI LLLCLIFLLV LLDCQGMLPV CPLIPGSTTT STGPCRTCTT   300
PAQGNSMFPS CCCTKPTDGN CTCIPIPSSW AFAKYLWEWA SVRFSWLSLL VPFVQWFVGL   360
SPTVWLSVIW MMYWGPSLY NILSPFIPLL PIFFCLWVYI                          400

SEQ ID NO: 22           moltype = AA   length = 108
FEATURE                 Location/Qualifiers
REGION                  1..108
                        note = Synthetic peptide
source                  1..108
                        mol_type = protein
                        organism = synthetic construct
SEQUENCE: 22
MGGWSSKPRK GMGTNLSVPN PLGFFPDHQL DPAFKANSEN PDWDLNPHKD NWPDAHKVGV    60
GAFGPGFTPP HGGLLGWSPQ AQGILTSVPA APPPASTNRQ SGRQPTPL                108

SEQ ID NO: 23           moltype = AA   length = 55
FEATURE                 Location/Qualifiers
REGION                  1..55
                        note = Synthetic peptide
source                  1..55
                        mol_type = protein
                        organism = synthetic construct
SEQUENCE: 23
SPPLRDTHPQ AMQWNSTTFH QTLQDPRVRA LYLPAGGSSS GTVSPAQNTV SAISS         55

SEQ ID NO: 24           moltype = AA   length = 237
FEATURE                 Location/Qualifiers
REGION                  1..237
                        note = Synthetic peptide
SITE                    94
                        note = misc_feature - Xaa can be any naturally occurring
                         amino acid
source                  1..237
                        mol_type = protein
                        organism = synthetic construct
SEQUENCE: 24
ILSTTGDPVP NMENIASGLL GPLLVLQAGF FSLTKILTIP QSLDSWWTSL SFLGGTPVCL    60
GQNSQSPISS HSPTCCPPIC PGYRWMYLRR FIIXLCILLL CLIFLLVLLD YQGMLPVCPL   120
IPGSSTTSTG PCKTCTTPAQ GTSMFPSCCC TKPTDGNCTC IPIPSSWAFA KYLWEWASVR   180
FSWLSLLVPF VQWFVGLSPT VWLSVIWMMW YWGPSLYNIL SPFMPLLPIF FCLWVYI      237

SEQ ID NO: 25           moltype = AA   length = 292
FEATURE                 Location/Qualifiers
REGION                  1..292
                        note = Synthetic peptide
SITE                    149
                        note = misc_feature - Xaa can be any naturally occurring
                         amino acid
source                  1..292
                        mol_type = protein
                        organism = synthetic construct
SEQUENCE: 25
SPPLRDTHPQ AMQWNSTTFH QTLQDPRVRA LYLPAGGSSS GTVSPAQNTV SAISSILSTT    60
GDPVPNMENI ASGLLGPLLV LQAGFFSLTK ILTIPQSLDS WWTSLSFLGG TPVCLGQNSQ   120
SPISSHSPTS CPPICPGYRW MYLRRFIIXL CILLLCLIFL LVLLDYQGML PVCPLIPGSS   180
TTSTGPCKTC TTPAQGTSMF PSCCCTKPTD GNCTCIPIPS SWAFAKYLWE WASVRFSWLS   240
LLVPFVQWFV GLSPTVWLSV IWMMYWGPS LYNILSPFMP LLPIFFCLWV YI            292
```

```
SEQ ID NO: 26           moltype = AA   length = 400
FEATURE                 Location/Qualifiers
REGION                  1..400
                        note = Synthetic peptide
SITE                    257
                        note = misc_feature - Xaa can be any naturally occurring
                         amino acid
source                  1..400
                        mol_type = protein
                        organism = synthetic construct
SEQUENCE: 26
MGGWSSKPRK GMGTNLSVPN PLGFFPDHQL DPAFKANSEN PDWDLNPHKD NWPDAHKVGV  60
GAFGPGFTPP HGGLLGWSPQ AQGILTSVPA APPPASTNRQ SGRQPTPLSP PLRDTHPQAM 120
QWNSTTFHQT LQDPRVRALY LPAGGSSSGT VSPAQNTVSA ISSILSTTGD PVPNMENIAS 180
GLLGPLLVLQ AGFFSLTKIL TIPQSLDSWW TSLSFLGGTP VCLGQNSQSP ISSHSPTCCP 240
PICPGYRWMY LRRFIIXLCI LLLCLIFLLV LLDYQGMLPV CPLIPGSSTT STGPCKTCTT 300
PAQGTSMFPS CCCTKPTDGN CTCIPIPSSW AFAKYLWEWA SVRFSWLSLL VPFVQWFVGL 360
SPTVWLSVIW MMWYWGPSLY NILSPFMPLL PIFFCLWVYI                      400

SEQ ID NO: 27           moltype = AA   length = 108
FEATURE                 Location/Qualifiers
REGION                  1..108
                        note = Synthetic peptide
source                  1..108
                        mol_type = protein
                        organism = synthetic construct
SEQUENCE: 27
MGGWSSKPRK GMGTNLSVPN PLGFFPDHQL DPAFKANSEN PDWDLNPHKD NWPDANKVGV  60
GAFGPGFTPP HGGLLGWSPQ AQGLLTTVPA APPPASTNRQ SGRQPTPL             108

SEQ ID NO: 28           moltype = AA   length = 55
FEATURE                 Location/Qualifiers
REGION                  1..55
                        note = Synthetic peptide
source                  1..55
                        mol_type = protein
                        organism = synthetic construct
SEQUENCE: 28
SPPLRDTHPQ AMQWNSTTFH QTLQDPRVRA LYFPAGGSSS GTVSPAQNTV STISS      55

SEQ ID NO: 29           moltype = AA   length = 237
FEATURE                 Location/Qualifiers
REGION                  1..237
                        note = Synthetic peptide
source                  1..237
                        mol_type = protein
                        organism = synthetic construct
SEQUENCE: 29
ILSKTGDPVP NMENIASGLL GPLLVLQAGF FLLTKILTIP QSLDSWWTSL NFLGGTPVCL  60
GQNSQSQISS HSPTCCPPIC PGYRWMCLRR FIIFLCILLL CLIFLLVLLD YQGMLPVCPL 120
IPGSSTTSTG PCKTCTTPAQ GTSMFPSCCC TKPTDGNCTC IPIPSSWAFA KYLWEWASVR 180
FSWLSLLVPF VQWFVGLSPT VWLSVIWMMW FWGPSLYNIL SPFMPLLPIF FCLWVYI    237

SEQ ID NO: 30           moltype = AA   length = 292
FEATURE                 Location/Qualifiers
REGION                  1..292
                        note = Synthetic peptide
source                  1..292
                        mol_type = protein
                        organism = synthetic construct
SEQUENCE: 30
SPPLRDTHPQ AMQWNSTTFH QTLQDPRVRA LYFPAGGSSS GTVSPAQNTV STISSILSKT  60
GDPVPNMENI ASGLLGPLLV LQAGFFLLTK ILTIPQSLDS WWTSLNFLGG TPVCLGQNSQ 120
SQISSHSPTC CPPICPGYRW MCLRRFIIFL CILLLCLIFL LVLLDYQGML PVCPLIPGSS 180
TTSTGPCKTC TTPAQGTSMF PSCCCTKPTD GNCTCIPIPS SWAFAKYLWE WASVRFSWLS 240
LLVPFVQWFV GLSPTVWLSV IWMMWFWGPS LYNILSPFMP LLPIFFCLWV YI         292

SEQ ID NO: 31           moltype = AA   length = 400
FEATURE                 Location/Qualifiers
REGION                  1..400
                        note = Synthetic peptide
source                  1..400
                        mol_type = protein
                        organism = synthetic construct
SEQUENCE: 31
MGGWSSKPRK GMGTNLSVPN PLGFFPDHQL DPAFKANSEN PDWDLNPHKD NWPDANKVGV  60
GAFGPGFTPP HGGLLGWSPQ AQGLLTTVPA APPPASTNRQ SGRQPTPLSP PLRDTHPQAM 120
QWNSTTFHQT LQDPRVRALY FPAGGSSSGT VSPAQNTVST ISSILSKTGD PVPNMENIAS 180
```

```
GLLGPLLVLQ  AGFFLLTKIL  TIPQSLDSWW  TSLNFLGGTP  VCLGQNSQSQ  ISSHSPTCCP   240
PICPGYRWMC  LRRFIIFLCI  LLLCLIFLLV  LLDYQGMLPV  CPLIPGSSTT  STGPCKTCTT   300
PAQGTSMFPS  CCCTKPTDGN  CTCIPIPSSW  AFAKYLWEWA  SVRFSWLSLL  VPFVQWFVGL   360
SPTVWLSVIW  MMWFWGPSLY  NILSPFMPLL  PIFFCLWVYI                          400

SEQ ID NO: 32              moltype = AA   length = 108
FEATURE                    Location/Qualifiers
REGION                     1..108
                           note = Synthetic peptide
source                     1..108
                           mol_type = protein
                           organism = synthetic construct
SEQUENCE: 32
MGGWSSKPRQ  GMGTNLSVPN  PLGFFPDHQL  DPAFGANSNN  PDWDFNPNKD  HWPEANQVGA    60
GAFGPGFTPP  HGGLLGWSPQ  AQGILTTLPA  APPPASTNRQ  SGRQPTPI                 108

SEQ ID NO: 33              moltype = AA   length = 55
FEATURE                    Location/Qualifiers
REGION                     1..55
                           note = Synthetic peptide
source                     1..55
                           mol_type = protein
                           organism = synthetic construct
SEQUENCE: 33
SPPLRDSHPQ  AMQWNSTTFH  QALLDPRVRG  LYFPAGGSSS  GTVNPVPTTA  SPISS         55

SEQ ID NO: 34              moltype = AA   length = 237
FEATURE                    Location/Qualifiers
REGION                     1..237
                           note = Synthetic peptide
source                     1..237
                           mol_type = protein
                           organism = synthetic construct
SEQUENCE: 34
IFSRTGDPAP  NMESTTSGFL  GPLLVLQAGF  FLLTRILTIP  QSLDSWWTSL  NFLGGAPTCP    60
GQNSQSPTSN  HSPTSCPPTC  PGYRWMCLRR  FIIFLFILLL  CLIFLLVLLD  YQGMLPVCPL   120
LPGTSTTSTG  PCRTCTIPAQ  GTSMFPSCCC  TKPSDGNCTC  IPIPSSWAFA  RFLWEWASVR   180
FSWLSLLVPF  VQWFVGLSPT  VWLSAIWMMW  YWGPSLYNIL  SPFLPLLPIF  FCLWVYI      237

SEQ ID NO: 35              moltype = AA   length = 292
FEATURE                    Location/Qualifiers
REGION                     1..292
                           note = Synthetic peptide
source                     1..292
                           mol_type = protein
                           organism = synthetic construct
SEQUENCE: 35
SPPLRDSHPQ  AMQWNSTTFH  QALLDPRVRG  LYFPAGGSSS  GTVNPVPTTA  SPISSIFSRT    60
GDPAPNMEST  TSGFLGPLLV  LQAGFFLLTR  ILTIPQSLDS  WWTSLNFLGG  APTCPGQNSQ   120
SPTSNHSPTS  CPPTCPGYRW  MCLRRFIIFL  FILLLCLIFL  LVLLDYQGML  PVCPLLPGTS   180
TTSTGPCRTC  TIPAQGTSMF  PSCCCTKPSD  GNCTCIPIPS  SWAFARFLWE  WASVRFSWLS   240
LLVPFVQWFV  GLSPTVWLSA  IWMMWYWGPS  LYNILSPFLP  LLPIFFCLWV  YI           292

SEQ ID NO: 36              moltype = AA   length = 400
FEATURE                    Location/Qualifiers
REGION                     1..400
                           note = Synthetic peptide
source                     1..400
                           mol_type = protein
                           organism = synthetic construct
SEQUENCE: 36
MGGWSSKPRQ  GMGTNLSVPN  PLGFFPDHQL  DPAFGANSNN  PDWDFNPNKD  HWPEANQVGA    60
GAFGPGFTPP  HGGLLGWSPQ  AQGILTTLPA  APPPASTNRQ  SGRQPTPISP  PLRDSHPQAM   120
QWNSTTFHQA  LLDPRVRGLY  FPAGGSSSGT  VNPVPTTASP  ISSIFSRTGD  PAPNMESTTS   180
GFLGPLLVLQ  AGFFLLTRIL  TIPQSLDSWW  TSLNFLGGAP  TCPGQNSQSP  TSNHSPTSCP   240
PTCPGYRWMC  LRRFIIFLFI  LLLCLIFLLV  LLDYQGMLPV  CPLLPGTSTT  STGPCRTCTI   300
PAQGTSMFPS  CCCTKPSDGN  CTCIPIPSSW  AFARFLWEWA  SVRFSWLSLL  VPFVQWFVGL   360
SPTVWLSAIW  MMWYWGPSLY  NILSPFLPLL  PIFFCLWVYI                          400

SEQ ID NO: 37              moltype = AA   length = 97
FEATURE                    Location/Qualifiers
REGION                     1..97
                           note = Synthetic peptide
source                     1..97
                           mol_type = protein
                           organism = synthetic construct
SEQUENCE: 37
MGQNLSTSNP  LGFFPDHQLD  PAFRANTANP  DWDFNPNKDT  WPDANKVGAG  AFGLGFTPPH    60
GGLLGWSPQA  QGILQTLPAN  PPPASTNRQS  GRQPTPL                               97
```

```
SEQ ID NO: 38              moltype = AA   length = 55
FEATURE                    Location/Qualifiers
REGION                     1..55
                           note = Synthetic peptide
source                     1..55
                           mol_type = protein
                           organism = synthetic construct
SEQUENCE: 38
SPPLRNTHPQ AMQWNSTTFH QTLQDPRVRG LYFPAGGSSS GTVNPVLTTA SPLSS       55

SEQ ID NO: 39              moltype = AA   length = 237
FEATURE                    Location/Qualifiers
REGION                     1..237
                           note = Synthetic peptide
source                     1..237
                           mol_type = protein
                           organism = synthetic construct
SEQUENCE: 39
IFSRIGDPAL NMENITSGFL GPLLVLQAGF FLLTRILTIP QSLDSWWTSL NFLGGTTVCL    60
GQNSQSPTSN HSPTSCPPTC PGYRWMCLRR FIIFLFILLL CLIFLLVLLD YQGMLPVCPL   120
IPGSSTTSTG PCRTCMTTAQ GTSMYPSCCC TKPSDGNCTC IPIPSSWAFG KFLWEWASAR   180
FSWLSLLVPF VQWFVGLSPT VWLSVIWMMW YWGPSLYSIL SPFLPLLPIF FCLWVYI      237

SEQ ID NO: 40              moltype = AA   length = 292
FEATURE                    Location/Qualifiers
REGION                     1..292
                           note = Synthetic peptide
source                     1..292
                           mol_type = protein
                           organism = synthetic construct
SEQUENCE: 40
SPPLRNTHPQ AMQWNSTTFH QTLQDPRVRG LYFPAGGSSS GTVNPVLTTA SPLSSIFSRI    60
GDPALNMENI TSGFLGPLLV LQAGFFLLTR ILTIPQSLDS WWTSLNFLGG TTVCLGQNSQ   120
SPTSNHSPTS CPPTCPGYRW MCLRRFIIFL FILLLCLIFL LVLLDYQGML PVCPLIPGSS   180
TTSTGPCRTC MTTAQGTSMY PSCCCTKPSD GNCTCIPIPS SWAFGKFLWE WASARFSWLS   240
LLVPFVQWFV GLSPTVWLSV IWMMWYWGPS LYSILSPFLP LLPIFFCLWV YI           292

SEQ ID NO: 41              moltype = AA   length = 389
FEATURE                    Location/Qualifiers
REGION                     1..389
                           note = Synthetic peptide
source                     1..389
                           mol_type = protein
                           organism = synthetic construct
SEQUENCE: 41
MGQNLSTSNP LGFFPDHQLD PAFRANTANP DWDFNPNKDT WPDANKVGAG AFGLGFTPPH    60
GGLLGWSPQA QGILQTLPAN PPPASTNRQS GRQPTPLSPP LRNTHPQAMQ WNSTTFHQTL   120
QDPRVRGLYF PAGGSSSGTV NPVLTTASPL SSIFSRIGDP ALNMENITSG FLGPLLVLQA   180
GFFLLTRILT IPQSLDSWWT SLNFLGGTTV CLGQNSQSPT SNHSPTSCPP TCPGYRWMCL   240
RRFIIFLFIL LLCLIFLLVL LDYQGMLPVC PLIPGSSTTS TGPCRTCMTT AQGTSMYPSC   300
CCTKPSDGNC TCIPIPSSWA FGKFLWEWAS ARFSWLSLLV PFVQWFVGLS PTVWLSVIWM   360
MWYWGPSLYS ILSPFLPLLP IFFCLWVYI                                    389

SEQ ID NO: 42              moltype = AA   length = 107
FEATURE                    Location/Qualifiers
REGION                     1..107
                           note = Synthetic peptide
source                     1..107
                           mol_type = protein
                           organism = synthetic construct
SEQUENCE: 42
MGLSWTVPLE WGKNISTTNP LGFFPDHQLD PAFRANTRNP DWDHNPNKDH WTEANKVGVG    60
AFGPGFTPPH GGLLGWSPQA QGMLKTLPAD PPPASTNRQS GRQPTPI                 107

SEQ ID NO: 43              moltype = AA   length = 55
FEATURE                    Location/Qualifiers
REGION                     1..55
                           note = Synthetic peptide
source                     1..55
                           mol_type = protein
                           organism = synthetic construct
SEQUENCE: 43
TPPLRDTHPQ AMQWNSTTFH QALQDPRVRG LYFPAGGSSS GTVNPVPTTA SLISS        55

SEQ ID NO: 44              moltype = AA   length = 237
FEATURE                    Location/Qualifiers
REGION                     1..237
                           note = Synthetic peptide
```

```
source                          1..237
                                mol_type = protein
                                organism = synthetic construct
SEQUENCE: 44
IFSRIGDPAP NMESITSGFL GPLLVLQAGF FLLTKILTIP QSLDSWWTSL NFLGGAPVCL      60
GQNSQSPTSN HSPTSCPPIC PGYRWMCLRR FIIFLFILLL CLIFLLVLLD YQGMLPVCPL     120
IPGSSTTSTG PCRTCMTLAQ GTSMFPSCCC SKPSDGNCTC IPIPSSWAFG KFLWEWASAR     180
FSWLSLLVPF VQWFAGLSPT VWLSVIWMMW YWGPSLYDIL SPFIPLLPIF FCLWVYI        237

SEQ ID NO: 45                   moltype = AA   length = 292
FEATURE                         Location/Qualifiers
REGION                          1..292
                                note = Synthetic peptide
source                          1..292
                                mol_type = protein
                                organism = synthetic construct
SEQUENCE: 45
TPPLRDTHPQ AMQWNSTTFH QALQDPRVRG LYFPAGGSSS GTVNPVPTTA SLISSIFSRI      60
GDPAPNMESI TSGFLGPLLV LQAGFFLLTK ILTIPQSLDS WWTSLNFLGG APVCLGQNSQ     120
SPTSNHSPTS CPPICPGYRW MCLRRFIIFL FILLLCLIPL LVLLDYQGML PVCPLIPGSS     180
TTSTGPCRTC MTLAQGTSMF PSCCCSKPSD GNCTCIPIPS SWAFGKFLWE WASARFSWLS     240
LLVPFVQWFA GLSPTVWLSV IWMMYWGPS LYDILSPFIP LLPIFFCLWV YI              292

SEQ ID NO: 46                   moltype = AA   length = 399
FEATURE                         Location/Qualifiers
REGION                          1..399
                                note = Synthetic peptide
source                          1..399
                                mol_type = protein
                                organism = synthetic construct
SEQUENCE: 46
MGLSWTVPLE WGKNISTTNP LGFFPDHQLD PAFRANTRNP DWDHNPNKDH WTEANKVGVG      60
AFGPGFTPPH GGLLGWSPQA QGMLKTLPAD PPPASTNRQS GRQPTPITPP LRDTHPQAMQ     120
WNSTTFHQAL QDPRVRGLYF PAGGSSSGTV NPVPTTASLI SSIFSRIGDP APNMESITSG     180
FLGPLLVLQA GFFLLTKILT IPQSLDSWWT SLNFLGGAPV CLGQNSQSPT SNHSPTSCPP     240
ICPGYRWMCL RRFIIFLFIL LLCLIFLLVL LDYQGMLPVC PLIPGSSTTS TGPCRTCMTL     300
AQGTSMFPSC CCSKPSDGNC TCIPIPSSWA FGKFLWEWAS ARFSWLSLLV PFVQWFAGLS     360
PTVWLSVIWM MWYWGPSLYD ILSPFIPLLP IFFCLWVYI                            399

SEQ ID NO: 47                   moltype = AA   length = 108
FEATURE                         Location/Qualifiers
REGION                          1..108
                                note = Synthetic peptide
source                          1..108
                                mol_type = protein
                                organism = synthetic construct
SEQUENCE: 47
MGAPLSTTRR GMGQNLSVPN PLGFFPDHQL DPLFRANSSS PDWDFNKNKD NWPMANKVGV      60
GGYGPGFTPP HGGLLGWSPQ AQGVLTTLPA DPPPASTNRR SGRKPTPV                  108

SEQ ID NO: 48                   moltype = AA   length = 55
FEATURE                         Location/Qualifiers
REGION                          1..55
                                note = Synthetic peptide
source                          1..55
                                mol_type = protein
                                organism = synthetic construct
SEQUENCE: 48
SPPLRDTHPQ AMQWNSTQFH QALLDPRVRA LYFPAGGSSS ETQNPAPTIA SLTSS            55

SEQ ID NO: 49                   moltype = AA   length = 237
FEATURE                         Location/Qualifiers
REGION                          1..237
                                note = Synthetic peptide
source                          1..237
                                mol_type = protein
                                organism = synthetic construct
SEQUENCE: 49
IFLKTGGPAT NMDNITSGLL GPLLVLQAVC FLLTKILTIP QSLDSWWTSL NFLGGTPGCP      60
GQNSQSPTSN HLPTSCPPTC PGYRWMCLRR FIIFLFILLL CLIFLLVLVD YQGMLPVCPP     120
LPGSTTTSTG PCKTCTTLAQ GTSMFPSCCC SKPSDGNCTC IPIPSSWALG KYLWEWASAR     180
FSWLSLLVQF VQWCVGLSPT VWLLVIWMIW YWGPNLCSIL SPFIPLLPIF CYLWVSI        237

SEQ ID NO: 50                   moltype = AA   length = 292
FEATURE                         Location/Qualifiers
REGION                          1..292
                                note = Synthetic peptide
source                          1..292
                                mol_type = protein
```

```
                            organism = synthetic construct
SEQUENCE: 50
SPPLRDTHPQ  AMQWNSTQFH  QALLDPRVRA  LYFPAGGSSS  ETQNPAPTIA  SLTSSIFLKT   60
GGPATNMDNI  TSGLLGPLLV  LQAVCFLLTK  ILTIPQSLDS  WWTSLNFLGG  TPGCPGQNSQ  120
SPTSNHLPTS  CPPTCPGYRW  MCLRRFIIFL  FILLLCLIFL  LVLVDYQGML  PVCPPLPGST  180
TTSTGPCKTC  TTLAQGTSMF  PSCCCSKPSD  GNCTCIPIPS  SWALGKYLWE  WASARFSWLS  240
LLVQFVQWCV  GLSPTVWLLV  IWMIWYWGPN  LCSILSPFIP  LLPIFCYLWV  SI          292

SEQ ID NO: 51               moltype = AA  length = 400
FEATURE                     Location/Qualifiers
REGION                      1..400
                            note = Synthetic peptide
source                      1..400
                            mol_type = protein
                            organism = synthetic construct
SEQUENCE: 51
MGAPLSTTRR  GMGQNLSVPN  PLGFFPDHQL  DPLFRANSSS  PDWDFNKNKD  NWPMANKVGV   60
GGYGPGFTPP  HGGLLGWSPQ  AQGVLTTLPA  DPPPASTNRR  SGRKPTPVSP  PLRDTHPQAM  120
QWNSTQFHQA  LLDPRVRALY  FPAGGSSSET  QNPAPTIASL  TSSIFLKTGG  PATNMDNITS  180
GLLGPLLVLQ  AVCFLLTKIL  TIPQSLDSWW  TSLNFLGGTP  GCPGQNSQSP  TSNHLPTSCP  240
PTCPGYRWMC  LRRFIIFLFI  LLLCLIFLLV  LVDYQGMLPV  CPPLPGSTTT  STGPCKTCTT  300
LAQGTSMFPS  CCCSKPSDGN  CTCIPIPSSW  ALGKYLWEWA  SARFSWLSLL  VQFVQWCVGL  360
SPTVWLLVIW  MIWYWGPNLC  SILSPFIPLL  PIFCYLWVSI                          400

SEQ ID NO: 52               moltype = AA  length = 108
FEATURE                     Location/Qualifiers
REGION                      1..108
                            note = Synthetic peptide
source                      1..108
                            mol_type = protein
                            organism = synthetic construct
SEQUENCE: 52
MGAPLSTTRR  GMGQNLSVPN  PLGFFPEHQL  DPLFRANSSS  PDWDFNKNKD  TWPMANKVGV   60
GGYGPGFTPP  HGGLLGWSPQ  AQGVLTTLPA  DPPPASTNRR  SGRKPTPV                108

SEQ ID NO: 53               moltype = AA  length = 55
FEATURE                     Location/Qualifiers
REGION                      1..55
                            note = Synthetic peptide
source                      1..55
                            mol_type = protein
                            organism = synthetic construct
SEQUENCE: 53
SPPLRDTHPQ  AMQWNSTQFH  QALLDPRVRA  LYFPAGGSSS  ETQNPAPTIA  SLTSS        55

SEQ ID NO: 54               moltype = AA  length = 237
FEATURE                     Location/Qualifiers
REGION                      1..237
                            note = Synthetic peptide
source                      1..237
                            mol_type = protein
                            organism = synthetic construct
SEQUENCE: 54
IFSKTGGPAM  NMDSITSGLL  GPLLVLQAVC  FLLTKILTIP  QSLDSWWTSL  NFLGGLPGCP   60
GQNSQSPTSN  HLPTSCPPTC  PGYRWMCLRR  FIIFLFILLL  CLIFLLVLLD  YQGMLPVCPL  120
IPGSTTTSTG  PCKTCTTLAQ  GTSMFPSCCC  SKPSDGNCTC  IPIPSSWALG  KYLWEWASAR  180
FSWLSLLVQF  VQWCVGLSPT  VWLLVIWMIW  YWGPNLCSIL  SPFIPLLPIF  CYLWVSI     237

SEQ ID NO: 55               moltype = AA  length = 292
FEATURE                     Location/Qualifiers
REGION                      1..292
                            note = Synthetic peptide
source                      1..292
                            mol_type = protein
                            organism = synthetic construct
SEQUENCE: 55
SPPLRDTHPQ  AMQWNSTQFH  QALLDPRVRA  LYFPAGGSSS  ETQNPAPTIA  SLTSSIFSKT   60
GGPAMNMDSI  TSGLLGPLLV  LQAVCFLLTK  ILTIPQSLDS  WWTSLNFLGG  LPGCPGQNSQ  120
SPTSNHLPTS  CPPTCPGYRW  MCLRRFIIFL  FILLLCLIFL  LVLLDYQGML  PVCPLIPGST  180
TTSTGPCKTC  TTLAQGTSMF  PSCCCSKPSD  GNCTCIPIPS  SWALGKYLWE  WASARFSWLS  240
LLVQFVQWCV  GLSPTVWLLV  IWMIWYWGPN  LCSILSPFIP  LLPIFCYLWV  SI          292

SEQ ID NO: 56               moltype = AA  length = 400
FEATURE                     Location/Qualifiers
REGION                      1..400
                            note = Synthetic peptide
source                      1..400
                            mol_type = protein
                            organism = synthetic construct
```

```
SEQUENCE: 56
MGAPLSTTRR  GMGQNLSVPN  PLGFFPEHQL  DPLFRANSSS  PDWDFNKNKD  TWPMANKVGV   60
GGYGPGFTPP  HGGLLGWSPQ  AQGVLTTLPA  DPPPASTNRR  SGRKPTPVSP  PLRDTHPQAM  120
QWNSTQFHQA  LLDPRVRALY  FPAGGSSSET  QNPAPTIASL  TSSIFSKTGG  PAMNMDSITS  180
GLLGPLLVLQ  AVCFLLTKIL  TIPQSLDSWW  TSLNFLGGLP  GCPGQNSQSP  TSNHLPTSCP  240
PTCPGYRWMC  LRRFIIFLFI  LLLCLIFLLV  LLDYQGMLPV  CPLIPGSTTT  STGPCKTCTT  300
LAQGTSMFPS  CCCSKPSDGN  CTCIPIPSSW  ALGKYLWEWA  SARFSWLSLL  VQFVQWCVGL  360
SPTVWLLVIW  MIWYWGPNLC  SILSPFIPLL  PIFCYLWVSI                          400

SEQ ID NO: 57           moltype = AA   length = 107
FEATURE                 Location/Qualifiers
REGION                  1..107
                        note = Synthetic peptide
source                  1..107
                        mol_type = protein
                        organism = synthetic construct
SEQUENCE: 57
MGLSWTVPLE  WGKNLSASNP  LGFLPDHQLD  PAFRANTNNP  DWDFNPKKDP  WPEANKVGVG   60
AYGPGFTPPH  GGLLGWSPQS  QGTLTTLPAD  PPPASTNRQS  GRQPTPI                 107

SEQ ID NO: 58           moltype = AA   length = 55
FEATURE                 Location/Qualifiers
REGION                  1..55
                        note = Synthetic peptide
source                  1..55
                        mol_type = protein
                        organism = synthetic construct
SEQUENCE: 58
SPPLRDSHPQ  AMQWNSTAFH  QALQNPKVRG  LYFPAGGSSS  GIVNPVPTIA  SHISS        55

SEQ ID NO: 59           moltype = AA   length = 237
FEATURE                 Location/Qualifiers
REGION                  1..237
                        note = Synthetic peptide
source                  1..237
                        mol_type = protein
                        organism = synthetic construct
SEQUENCE: 59
IFSRIGDPAP  NMENITSGFL  GPLLVLQAGF  FLLTRILTIP  QSLDSWWTSL  NFLGGVPVCP   60
GLNSQSPTSN  HSPISCPPTC  PGYRWMCLRR  FIIFLFILLL  CLIFLLVLLD  YQGMLPVCPL  120
IPGSSTTSTG  PCKTCTTPAQ  GNSMYPSCCC  TKPSDGNCTC  IPIPSSWAFA  KYLWEWASVR  180
FSWLSLLVPF  VQWFVGLSPT  VWLSAIWMMW  YWGPNLYNIL  SPFIPLLPIF  FCLWVYI     237

SEQ ID NO: 60           moltype = AA   length = 292
FEATURE                 Location/Qualifiers
REGION                  1..292
                        note = Synthetic peptide
source                  1..292
                        mol_type = protein
                        organism = synthetic construct
SEQUENCE: 60
SPPLRDSHPQ  AMQWNSTAFH  QALQNPKVRG  LYFPAGGSSS  GIVNPVPTIA  SHISSIFSRI   60
GDPAPNMENI  TSGFLGPLLV  LQAGFFLLTR  ILTIPQSLDS  WWTSLNFLGG  VPVCPGLNSQ  120
SPTSNHSPIS  CPPTCPGYRW  MCLRRFIIFL  FILLLCLIFL  LVLLDYQGML  PVCPLIPGSS  180
TTSTGPCKTC  TTPAQGNSMY  PSCCCTKPSD  GNCTCIPIPS  SWAFAKYLWE  WASVRFSWLS  240
LLVPFVQWFV  GLSPTVWLSA  IWMMWYWGPN  LYNILSPFIP  LLPIFFCLWV  YI          292

SEQ ID NO: 61           moltype = AA   length = 399
FEATURE                 Location/Qualifiers
REGION                  1..399
                        note = Synthetic peptide
source                  1..399
                        mol_type = protein
                        organism = synthetic construct
SEQUENCE: 61
MGLSWTVPLE  WGKNLSASNP  LGFLPDHQLD  PAFRANTNNP  DWDFNPKKDP  WPEANKVGVG   60
AYGPGFTPPH  GGLLGWSPQS  QGTLTTLPAD  PPPASTNRQS  GRQPTPISPP  LRDSHPQAMQ  120
WNSTAPHQAL  QNPKVRGLYF  PAGGSSSGIV  NPVPTIASHI  SSIFSRIGDP  APNMENITSG  180
FLGPLLVLQA  GFFLLTRILT  IPQSLDSWWT  SLNFLGGVPV  CPGLNSQSPT  SNHSPISCPP  240
TCPGYRWMCL  RRFIIFLFIL  LLCLIFLLVL  LDYQGMLPVC  PLIPGSSTTS  TGPCKTCTTP  300
AQGNSMYPSC  CCTKPSDGNC  TCIPIPSSWA  FAKYLWEWAS  VRFSWLSLLV  PFVQWFVGLS  360
PTVWLSAIWM  MWYWGPNLYN  ILSPFIPLLP  IFFCLWVYI                           399

SEQ ID NO: 62           moltype = AA   length = 108
FEATURE                 Location/Qualifiers
REGION                  1..108
                        note = Synthetic peptide
source                  1..108
                        mol_type = protein
```

```
                        organism = synthetic construct
SEQUENCE: 62
MGAPLSTARR GMGQNLSVPN PLGFFPDHQL DPLFRANSSS PDWDFNTNKD NWPMANKVGV    60
GGFGPGFTPP HGGLLGWSPQ AQGILTTSPP DPPPASTNRR SGRKPTPV                108

SEQ ID NO: 63           moltype = AA   length = 55
FEATURE                 Location/Qualifiers
REGION                  1..55
                        note = Synthetic peptide
source                  1..55
                        mol_type = protein
                        organism = synthetic construct
SEQUENCE: 63
SPPLRDTHPQ AMQWNSTQFH QALLDPRVRG LYFPAGGSSS ETQNPAPTIA SLTSS         55

SEQ ID NO: 64           moltype = AA   length = 237
FEATURE                 Location/Qualifiers
REGION                  1..237
                        note = Synthetic peptide
source                  1..237
                        mol_type = protein
                        organism = synthetic construct
SEQUENCE: 64
IFSKTGDPAM NMENITSGLL RPLLVLQAVC FLLTKILTIP QSLDSWWTSL NFLGVPPGCP    60
GQNSQSPISN HLPTSCPPTC PGYRWMCLRR FIIFLFILLL CLIFLLVLLD YQGMLPVCPL   120
LPGSTTTSTG PCKTCTTLAQ GTSMFPSCCC TKPSDGNCTC IPIPSSWAFG KYLWEWASAR   180
FSWLSLLVQF VQWCVGLSPT VWLLVIWMIW YWGPNLCSIL SPFIPLLPIF CYLWASI     237

SEQ ID NO: 65           moltype = AA   length = 292
FEATURE                 Location/Qualifiers
REGION                  1..292
                        note = Synthetic peptide
source                  1..292
                        mol_type = protein
                        organism = synthetic construct
SEQUENCE: 65
SPPLRDTHPQ AMQWNSTQFH QALLDPRVRG LYFPAGGSSS ETQNPAPTIA SLTSSIFSKT    60
GDPAMNMENI TSGLLRPLLV LQAVCFLLTK ILTIPQSLDS WWTSLNFLGV PPGCPGQNSQ   120
SPISNHLPTS CPPTCPGYRW MCLRRFIIFL FILLLCLIFL LVLLDYQGML PVCPLLPGST   180
TTSTGPCKTC TTLAQGTSMF PSCCCTKPSD GNCTCIPIPS SWAFGKYLWE WASARFSWLS   240
LLVQFVQWCV GLSPTVWLLV IWMIWYWGPN LCSILSPFIP LLPIFCYLWA SI          292

SEQ ID NO: 66           moltype = AA   length = 400
FEATURE                 Location/Qualifiers
REGION                  1..400
                        note = Synthetic peptide
source                  1..400
                        mol_type = protein
                        organism = synthetic construct
SEQUENCE: 66
MGAPLSTARR GMGQNLSVPN PLGFFPDHQL DPLFRANSSS PDWDFNTNKD NWPMANKVGV    60
GGFGPGFTPP HGGLLGWSPQ AQGILTTSPP DPPPASTNRR SGRKPTPVSP PLRDTHPQAM   120
QWNSTQFHQA LLDPRVRGLY FPAGGSSSET QNPAPTIASL TSSIFSKTGD PAMNMENITS   180
GLLRPLLVLQ AVCFLLTKIL TIPQSLDSWW TSLNFLGVPP GCPGQNSQSP ISNHLPTSCP   240
PTCPGYRWMC LRRFIIFLFI LLLCLIFLLV LLDYQGMLPV CPLLPGSTTT STGPCKTCTT   300
LAQGTSMFPS CCCTKPSDGN CTCIPIPSSW AFGKYLWEWA SARFSWLSLL VQFVQWCVGL   360
SPTVWLLVIW MIWYWGPNLC SILSPFIPLL PIFCYLWASI                        400

SEQ ID NO: 67           moltype = AA   length = 703
FEATURE                 Location/Qualifiers
REGION                  1..703
                        note = Synthetic peptide
REGION                  1..20
                        note = MISC_FEATURE - Optional leader sequence
REGION                  21..129
                        note = MISC_FEATURE - G28-8VL
REGION                  130..149
                        note = MISC_FEATURE - Gly-Ser linker
REGION                  150..269
                        note = MISC_FEATURE - G28-8VH
REGION                  270..503
                        note = MISC_FEATURE - Hing-CH2-CH3
REGION                  504..533
                        note = MISC_FEATURE - Gly-Ser linker
REGION                  534..697
                        note = MISC_FEATURE - preS1/preS2
REGION                  698..703
                        note = MISC_FEATURE - Optional 6x-His
source                  1..703
```

```
                        mol_type = protein
                        organism = synthetic construct
SEQUENCE: 67
METPAQLLFL  LLLWLPDTTG  DIQMTQSPAS  LSASVGETVT  ITCRASEKIY  SYLAWYQQKQ   60
GKSPQLLVYN  AKTLAEGVPS  RFSVSGSGTQ  FSLRINSLQP  EDFGTYYCQH  HFGSPRTFGG  120
GTKLEIKDLG  GGGSGGGGSG  GGGSGGGGST  GEVQLQQSGP  ELVKPGASMK  ISCKASGYSF  180
TGYTMNWVKQ  SHGKTLEWIG  LINPYNGVTS  YNQKFKDKAT  LTVDKSSSTA  YMELLSLTSE  240
DSAIYYCARD  YNYDYFDYWG  QGTTLTVSSD  LEPKSSDKTH  TCPPCPAPEL  LGGSSVFLFP  300
PKPKDTLMIS  RTPEVTCVVV  DVSHEDPEVK  FNWYVDGVEV  HNAKTKPREE  QYNSTYRVVS  360
VLTVLHQDWL  NGKEYKCSVS  NKALPASIEK  TISKAKGQPR  EPQVYTLPPS  REEMTKNQVS  420
LTCLVKGFYP  SDIAVEWESN  GQPENNYKTT  PPVLDSDGSF  FLYSKLTVDK  SRWQQGNVFS  480
CSVMHEALHN  HYTQKSLSLS  PGKGGGGSGG  GGSGGGGSGG  GGSMGGWSSK  PRQGMGTNLS  540
VPNPLGFFPD  HQLDPAFGAN  SNNPDWDFNP  NKDHWPEANQ  VGAGAFGPGF  TPPHGGLLGW  600
SPQAQGILTT  LPAAPPPAST  NRQSGRQPTP  ISPPLRDSHP  QAMQWNSTTF  HQALLDPRVR  660
GLYFPAGGSS  SGTVNPVPTT  ASPISSIFSR  TGDPAPNHHH  HHH                     703

SEQ ID NO: 68           moltype = DNA  length = 2142
FEATURE                 Location/Qualifiers
misc_feature            1..2142
                        note = G28-8scAb-preS1-S2-His
source                  1..2142
                        mol_type = other DNA
                        organism = synthetic construct
SEQUENCE: 68
gcgaagcttt  gagccaccat  ggaaacccca  gcgcagcttc  tcttcctcct  gctactctgg    60
ctcccagata  ccaccggtga  catcccagatg actcagtctc  cagcctccct  atctgcatct   120
gtgggagaaa  ctgtcaccat  cacatgtcga  gcaagtgaga  agatttacag  ttatttagca   180
tggtatcagc  agaaacaggg  aaaatctcct  cagctcctgg  tctataacgc  aaaaacctta   240
gcagaaggtg  tgccatcaag  gttcagtgtc  agtggatcag  gcacacagtt  ttctctgagg   300
atcaacagcc  tgcagcctga  agattttggg  acttattact  gtcaacatca  ttttggttct   360
cctcggacgt  tcggtggagg  caccaaactg  gaaatcaaag  atctcggagg  aggtggctca   420
ggtggtggag  gatctggagg  aggtgggagt  ggtggaggtg  gttctaccgg  tgaggtccag   480
ctgcaacagt  ctggacctga  actggtgaag  cctggagctt  caatgaagat  atcctgcaag   540
gcttctggtt  actcattcac  tggctacacc  atgaactggg  tgaagcagag  ccatggaaag   600
acccttgaat  ggattggact  tattaatcct  tacaatggtg  ttactagcta  caaccagaag   660
ttcaaggaca  aggccacatt  aactgtagac  aagtcatcca  gcacagccta  catggaactc   720
ctcagtctga  catctgagga  ctctgcaatc  tattactgtg  caagagacta  taattacgac   780
tactttgact  actgggccca  aggcaccact  ctcacagtct  cctcagatct  cgagcccaaa   840
tcttctgaca  aaactcacac  atgtccaccg  tgtccagcac  ctgaactcct  gggtggatcg   900
tcagtcttcc  tcttcccccc  aaaacccaag  gacactctca  tgatctcccg  gacccctgag   960
gtcacgtgcg  tggtggtgga  cgtgagccac  gaagaccccg  aggtcaagtt  caactgtac   1020
gtggacggcg  tggaggtgca  taatgccaag  acaaagccac  gggaggagca  gtacaacagc  1080
acgtaccgtg  tggtcagcgt  cctcaccgtc  ttgcaccagg  actggctgaa  cggcaaggag  1140
tacaagtgct  cggtctccaa  caaagccctc  ccagcctcca  tcgagaaaac  aatctccaaa  1200
gccaaagggc  agccccgaga  accacaggtg  tacaccctgc  ccccatcccg  ggaggagatg  1260
accaagaacc  aggtcagcct  gacctgcctg  gtcaaaggct  tctatcccag  cgacatcgcc  1320
gtggagtggg  agagcaatgg  gcagccggag  aacaactaca  agaccacgcc  tcccgtgctg  1380
gactccgacg  gctccttctt  cctctacagc  aagctcaccg  tggacaagag  caggtggcag  1440
caggggaacg  tcttctcatg  ctccgtgatg  catgaggctc  tgcacaacca  ctacacgcag  1500
aagagcctct  ctctgtctcc  gggtaaagga  ggagtggct  caggtggtgg  aggatctgga  1560
ggaggtggga  gtggtggagg  tggttctatg  ggaggttggt  cttccaaacc  tcgacaaggc  1620
atggggacga  atcttctgt  tcccaatcct  ctggattctt  tcccgatca  ccagttggac  1680
cctgcgttcg  gagccaactc  aaacaattcca  gattgggact  tcaacccaa  caaggatcc  1740
tggccagagg  caaatcaggt  aggagcggga  gcatttggtc  cagggttcac  cccaccacac  1800
ggaggccttt  tgggtggag  ccctcaggct  cagggcatat  tgacaacact  gccagcagca  1860
cctcctcctg  cctccaccaa  tcggcagtca  ggaagacagc  ctactcccat  ctctccacct  1920
ctaagagaca  gtcatcctca  ggccatgcag  tggaactcca  acattcca  ccaagctctg  1980
ctagatccca  gagtgagggg  cctatatttt  cctgctggtg  gctccagttc  ggaacagta  2040
aaccctgttc  cgactactgc  ctcacccata  tcgtcaatct  tctcgaggac  tggggaccct  2100
gcaccgaacc  accaccatca  tcatcattga  taaggatccg  cg                      2142

SEQ ID NO: 69           moltype = AA  length = 20
FEATURE                 Location/Qualifiers
REGION                  1..20
                        note = Gly-Ser linker
source                  1..20
                        mol_type = protein
                        organism = synthetic construct
SEQUENCE: 69
GGGGSGGGGS  GGGGSGGGGS                                                    20
```

THERAPEUTIC VACCINE FOR HEPATITIS B VIRUS (HBV) USING THE HBV PreS1 AND/OR PreS2, AND/OR S-HBsAg REGIONS OF THE HBV ENVELOPE PROTEIN

CROSS-REFERENCE

This application is a Continuation of U.S. patent application Ser. No. 16/764,950, filed May 18, 2020, now U.S. Pat. No. 11,389,532 issued on Jul. 19, 2022, which is a U.S. national phase of International Application No. PCT/US2018/061218, filed on Nov. 15, 2018, which claims priority to U.S. Provisional Application No. 62/587,051, filed Nov. 16, 2017, all of which are incorporated by reference herein in their entirety.

STATEMENT OF GOVERNMENT RIGHTS

This disclosure was made with government support under Grant No. HR0011-11-2-0007, awarded by the Defense Advanced Research Projects Agency. The government has certain rights in the disclosure.

REFERENCE TO AN ELECTRONIC SEQUENCE LISTING

A computer readable form of the Sequence Listing is filed with this application by electronic submission and is incorporated into this application by reference in its entirety. The Sequence Listing is contained in the file created on Nov. 9, 2022 having the file name "17-1273-WO-US-CON.xml" and is 106 kb in size.

BACKGROUND OF THE DISCLOSURE

In spite of the availability of prophylactic Hepatitis B virus (HBV) vaccines, HBV infection remains a very significant global health problem in both industrialized and developing nations; it is second only to tobacco as a cause of cancer. There is a clear unmet need for a therapeutic HBV vaccine for patients chronically infected with HBV (CHB). 10-30% of those vaccinated with marketed HBV vaccines do not respond either due to genetic factors, or non-compliance (failure to return for a series of 3 vaccinations). Only 37% of individuals vaccinated once with a licensed HBV vaccine are protected; even after three vaccinations, which are difficult to achieve, many people do not respond effectively. There is no effective vaccine for the 400 million people chronically infected with HBV, including asymptomatic HBV carriers. The drugs currently used to treat CHB patients are problematic. Sustained antiviral responses are rarely achieved and the currently available therapies can lead to viral resistance and produce side effects in many CHB patients.

DETAILED DESCRIPTION OF THE DISCLOSURE

Figure 1:
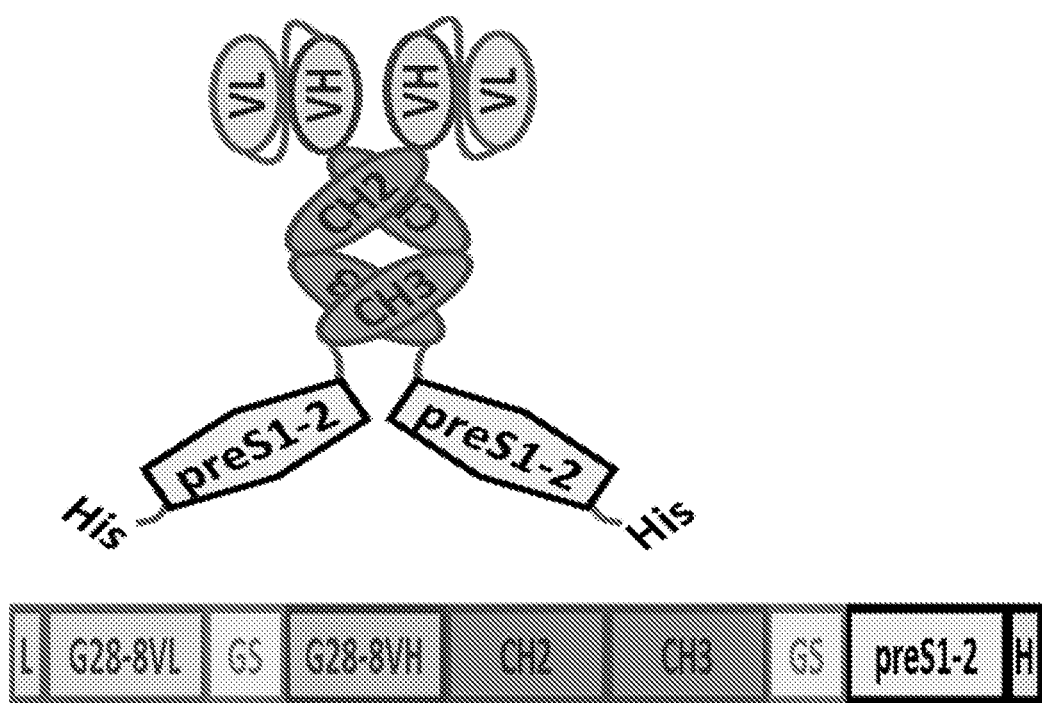
FIG. 1. Schematic design of the G28-8LH-scAb-PreS1-S2-His protein.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R. I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

In a first aspect, the present disclosure provides compositions, comprising:
 (a) a CD180 binding ligand; and
 (b) Hepatitis B virus pre-S1 and/or pre-S2 regions of the HBV envelope protein (HBVpreS1-S2Ag), S-HBsAg, or antigenic fragments or mutants thereof, attached to the CD180 binding ligand.

The compositions of the disclosure can be used, for example, to induce prophylactic responses in individuals at risk of HBV infection, and therapeutic responses in already infected individuals and in immunodeficient individuals who do not respond well to standard vaccines. The present disclosure is highly significant because it provides a therapeutic vaccine for one of the major causes of cancer and liver disease in the world: hepatitis B virus (HBV). HBV infection is a serious global public health problem in both industrialized and developing nations. 10-30 million people worldwide become infected with HBV each year, and more than 2 billion people worldwide have been infected with HBV. Significantly, the ability of unvaccinated individuals to mount effective immune responses against HBV is correlated with age. Infants and young children are particularly at risk, as 90% of infants and up to 50% of young children infected with HBV ultimately develop chronic infections. About 400 million are chronically infected with HBV (CHB), and in the USA there are approximately 1.4 million CHB infected people[5]. In the USA the prevalence of HBV while dropping in children, has changed little in adults[11] such that the burden of chronic hepatitis B among adults remains large; in some groups it is as high as 1%. An estimated 1 million people die each year from hepatitis and its complications, including about 5,000 people in the US. Of the 5000 persons in the United States who die each year from HBV related conditions, 300 die from fulminant hepatitis; 3-4000, from cirrhosis; and 600-1000, from primary hepatocellular carcinoma (HCC). In the US, approximately 400 health care workers are infected each year and are at risk from dying from HBV-related disease[16].

The CD180 binding ligand may be any molecule that binds directly to CD180 present in the surface of B cells, macrophages, or dendritic cells. In various non-limiting embodiments, the CD180 binding ligand may be a peptide mimetic or an antibody.

In a particular embodiment, the CD180 binding ligand is an antibody or antibody fragment. As used herein, "antibody" includes reference to full length and functional fragments of any of the following: an immunoglobulin molecule immunologically reactive with human CD180 (preferably selective for CD180), genetically engineered forms such as chimeric antibodies (e.g., humanized murine antibodies) and heteroconjugate antibodies (e.g., bispecific antibodies), fully humanized antibodies, human antibodies, single chain Fv fragments (scFv), bivalent or bispecific molecules, diabodies, triabodies, and tetrabodies, single domain molecules such as VH and VL that are capable of specifically binding to an epitope of an antigen, and camelids. Fragments with antigen-binding activity include, but are not limited to, Fab', $F(ab')_2$, Fab, Fv and rIgG and includes monoclonal antibodies. Various isotypes of antibodies exist, for example IgG1, IgG2, IgG3, IgG4, and other Ig, e.g., IgM, IgA, IgE isotypes. The term also includes. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:*5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301. Various antigen binding domain-fusion proteins are also disclosed, e.g., in US patent application Nos. 2003/0118592 and 2003/0133939, and are encompassed within the term "antibody" as used in this application.

An antibody immunologically reactive with human CD180 can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

In one embodiment, the CD180 binding ligand comprises a single chain (sc) recombinant protein, wherein the sc recombinant protein comprises:

(i) a variable heavy (VH) chain region of an anti-CD180 antibody; and (ii) a variable light (VL) chain region of an anti-CD180 antibody.

In one embodiment, the CD180 binding ligand comprises a single domain (sd) recombinant protein, wherein the sd recombinant protein comprises a variable heavy (VHH) chain region of an anti-CD180 antibody derived from a camelid species.

The VH and VL chain regions may be from an anti-human CD180 antibody, such as an anti-human CD180 monoclonal antibody. Exemplary commercially available CD180 anti-human monoclonal antibodies from which the VH and VL chains may be used include, but are not limited to, those sold by AbD Serotec™ ("MHR73-11"), BD Biosciences, Thermo Scientific, Sigma Aldrich, etc.), ("G28-8"), and LifeSpan™ ("200.1"). In one embodiment, the single chain recombinant protein does not include any other immunoglobulin domains (i.e.: a single chain variable fragment (scFv)). In an alternative embodiment, the single chain recombinant protein further comprises: CH2 and CH3 domains from an immunoglobulin (Ig), such as a human Ig, or functional mutants thereof, wherein the CH2 and CH3 domains are located C-terminal to the VH and VL domains. The CH2 and CH3 domains may be from any immunoglobulin as deemed appropriate for an intended use of the composition, including but not limited to IgA1, IgA2, IgG1, IgG2, IgG3, IgG4, IgM, etc. In a particular embodiment, the sc recombinant protein comprises CH2 and CH3 domains from IgG1, such as human IgG1, or functional mutants thereof. In a particular embodiment, such "functional mutants" comprise CH2 and/or CH3 domains that have impaired binding to human or animal Fc receptor FcγRIIb and/or to human or animal complement proteins (J Biol Chem 276: 6591-6604). The Fc domain of the recombinant molecules is an altered human IgG1 Fc domain with three amino acid changes (P238S, P331S, K322S) that reduce the binding of the molecule to Fc receptors and C1q. Other amino acid substitutions that can reduce binding of human IgG1 to various Fc receptors include but are not limited to E233P, L234V, L235A, G236 deletion, P238A, D265A, N297A, A327Q, and P329A. Substitutions at these amino acids reduce binding to all FcγR. Substitutions at D270A, Q295A, or A327S reduce binding to FcγRII and FcγRIIIA. Substitutions at S239A, E269A, E293A, Y296F, V303A, A327G, K338A, and D376A reduce binding to FcγRIIIA but not FcγRII. A combination of two of more of these substitutions can be engineered in the Fc domains of human IgG1 to achieve the desired effects on inhibiting Fc-FcγR interaction between CD180 targeted vaccines and FcgR expressing cells. Similarly, modifying the glycosylation profile of human IgG1, for example, substitution of the N-linked glycosylation site at Asn-297 of human IgG1, eliminates N-linked glycosylation of human IgG1, thereby eliminating its binding to Fc receptors as well as complement fixation functions (John S. Axford (ed.), Glycobiology and Medicine, 27-43; 2005 Springer).

In these various embodiments of the compositions of the disclosure, the VL chain region may be located N-terminal to the VH chain region, or the VH chain region may be located N-terminal to the VL chain region, as disclosed in the examples that follow.

In one embodiment, the CD180-antibody comprises mAb G28-8, which is commercially available from a number of sources, (BD Biosciences, Thermo Scientific, Sigma Aldrich, etc.), a F(ab')2 fragment of mAb G28-8, or a single chain recombinant protein having the VL and VH domains of G28-8, and optionally further comprising CH2 and CH3 domains from an immunoglobulin (Ig), such as a human Ig, or functional mutants thereof.

In another embodiment, the CD180 binding ligand competes for binding to CD180 with monoclonal antibody G28-8. As used herein, competing CD180 binding ligands are those binding proteins that bind to about, substantially or essentially the same, or even the same, epitope as G28-8. Competing binding proteins, such as competing antibodies or derivatives thereof, include binding proteins with overlapping epitope specificities. Competing binding proteins are thus able to effectively compete with G28-8 antibody, such as the G28-8 antibody obtained from Thermo Scientific (the "reference antibody") for binding to CD180. A binding protein that competes with the reference G28-8 antibody for binding to CD180 will be able to effectively or significantly reduce (i.e.: reduce by at least 10%; preferably by at least 20%, 30%, 40%, 50%, 60%, 70%, 80%, 90%, or more) reference G28-8 antibody binding to CD180, as evidenced by a reduction in bound label. In one embodiment, the reference G28-8 antibody is pre-mixed with varying amounts of the test binding proteins (e.g., 1:10, 1:100 or 1:1000) for a period of time prior to applying to a CD180 composition. In other embodiments, the reference G28-8 antibody and varying amounts of test binding proteins can simply be admixed during exposure to the CD180 composition. By using species or isotype secondary antibodies one will be able to detect only the bound reference G28-8 antibody, the binding of which will be reduced by the presence of a test binding protein that "competes" for binding. Examples of detection of such binding events are provided herein. As the identification of competing binding proteins is determined in comparison to the reference G28-8 antibody, it will be understood that actually determining the epitope to which the binding proteins bind is not in any way required in order to identify a competing binding proteins. However, epitope mapping can be performed, if desired.

In another embodiment, the CD180 binding ligand activates antigen-presenting cells, e.g., to increase expression of CD40, as shown in the examples that follow.

The compositions of the disclosure comprise a Hepatitis B virus preS1 and/or pre-S2 region of the envelope antigen (HBVpreS1/ S2Ag), an S-HBsAg, or antigenic fragments or mutants thereof (collectively referred to as HBVpreS1/ S2Ag or S-HBsAg) attached to the CD180 binding ligand. Thus, the compositions may comprise one or more HBVpreS1/ S2Ags and/or S-HBsAgs. In all embodiments, one or more copies of HBVpreS1/ S2Ags and/or S-HBsAgs may be present at the N-terminus or the C-terminus of the single chain recombinant protein. PreS1 and PreS2 are present in HBV surface antigens L-HBsAg and M-HBsAg and thus the HBVpreS1/ S2Ag may comprise isolated PreS1 and/or PreS2, or may comprise HBV L-HBsAg or M-HBsAg. The HBVpreS1/ S2Ag, L-HBsAg, M-HBsAg, and S-HBsAg may be from any HBV genotype, serotype, variant, mutant, or isolate.

In various embodiments, the composition may comprise an HBVpreS1/ S2Ag or S-HBsAg at least 90% identical over the length of the amino acid sequence of one or more of the following:

```
preS1/preS2
                                         (SEQ ID NO: 1)
MGGWSSKPRQ GMGTNLSVPN PLGFFPDHQL DPAFGANSNN

PDWDFNPNKD HWPEANQVGA GAFGPGFTPP HGGLLGWSPQ

AQGILTTLPA APPPASTNRQ SGRQPTPISP PLRDSHPQAM

QWNSTTFHQA LLDPRVRGLY FPAGGSSSGT VNPVPTTASP

ISSIFSRTGD PAPN preS1
                                         (SEQ ID NO: 2)
MGGWSSKPRQ GMGTNLSVPN PLGFFPDHQL DPAFGANSNN

PDWDFNPNKD HWPEANQVGA GAFGPGFTPP HGGLLGWSPQ

AQGILTTLPA APPPASTNRQ SGRQPTPI preS2
                                         (SEQ ID NO: 3)
SPPLRDSHPQA MQWNSTTFHQ ALLDPRVRGL YFPAGGSSSG

TVNPVPTTAS PISSIFSRTG DPAPN
```

L-HBsAg
(SEQ ID NO: 4)
MGGWSSKPRQ GMGTNLSVPN PLGFFPDHQL DPAFGANSNN
PDWDFNPNKD HWPEANQVGA GAFGPGFTPP HGGLLGWSPQ
AQGILTTLPA APPPASTNRQ SGRQPTPISP PLRDSHPQAM
QWNSTTFHQA LLDPRVRGLY FPAGGSSSGT VNPVPTTASP
ISSIFSRTGD PAPNMESTTS GFLGPLLVLQ AGFFLLTRIL
TIPQSLDSWW TSLNFLGGAP TCPGQNSQSP TSNHSPTSCP
PTCPGYRWMC LRRFIIFLFI LLLCLIFLLV LLDYQGMLPV
CPLLPGTSTT STGPCRTCTI PAQGTSMFPS CCCTKPSDGN
CTCIPIPSSW AFARFLWEWA SVRFSWLSLL VPFVQWFVGL
SPTVWLSAIW MMWYWGPSLY NILSPFLPLL PIFFCLWVYI M-HBsAg
(SEQ ID NO: 5)
PPLRDSHPQA MQWNSTTFHQ ALLDPRVRGL YFPAGGSSSG
TVNPVPTTAS PISSIFSRTG DPAPNMESTT SGFLGPLLVL
QAGFFLLTRI LTIPQSLDSW WTSLNFLGGA PTCPGQNSQS
PTSNHSPTSC PPTCPGYRWM CLRRFIIFLF ILLLCLIFLL
VLLDYQCMLP VCPLLPGTST TSTGPCRTCT IPAQGTSMFP
SCCCTKPSDG NCTCIPIPSS WAFARFLWEW ASVRFSWLSL
LVPFVQWFVG LSPTVWLSAI WMMWYWGPSL YNILSPFLPL
LPIFFCLWVY I S-HBsAg
(SEQ ID NO: 6)
MESTTSGFLG PLLVLQAGFF LLTRILTIPQ SLDSWWTSLN
FLGGAPTCPG QNSQSPTSNH SPTSCPPTCP GYRWMCLRRF
IIFLFILLLC LIFLLVLLDY QGMLPVCPLL PGTSTTSTGP
CRTCTIPAQG TSMFPSCCCT KPSDGNCTCI PIPSSWAFAR
FLWEWASVRF SWLSLLVPFV QWFVGLSPTV WLSAIWMMWY
WGPSLYNILS PFLPLLPIFF CLWVYI P31873 Hepatitis B Virus Genotype A1 Subtype Adw2 (Isolate Southern-Africa/Cai)

PreS1
(SEQ ID NO: 7)
MGGWSAKPRKGMGTNLSVPNPLGFFPDHQLDPAFGANSNN
PDWDFNPNKDHWPEANQVGVGAFGPGFTPPHGGLLGWSSQ
AQGTLHTVPAVPPPASTNRQTGRQPTPI

PreS2
(SEQ ID NO: 8)
SPPLRDSHPQAMQWNSTAFQQALQDPRVRGLFFPAGGSSSS
GTVNPAPNIASHISS

S-HBsAg
(SEQ ID NO: 9)
ISSRTGDPALNMENITSGFLGPLLVLQAGFFLLTRILTIP
QSLDSWWTSLNFLGGSPVCLGQNSQSPTSNHSPTSCPPIC
PGYRWMCLRRFIIFLFILLLCLIFLLVLLDYQGMLPVCPL
IPGSTTTSTGPCKTCTTPAQGNSMFPCCCTKPTDGNCTCI
PIPSSWAFAKYLWEWASVRFSWLSLLVPFVQWFVGLSPTV
WLSVIWMMWYWGPSLYNILSPFIPLLPIFFCLWVYI

M-HBsAg
(SEQ ID NO: 10)
SPPLRDSHPQAMQWNSTAFQQALQDPRVRGLFFPAGGSSS
GTVNPAPNIASHISSISSRTGDPALNMENITSGFLGPLLV
LQAGFFLLTRILTIPQSLDSWWTSLNFLGGSPVCLGQNSQ
SPTSNHSPTSCPPICPGYRWMCLRRFIIFLFILLLCLIFL
LVLLDYQGMLPVCPLIPGSTTTSTGPCKTCTTPAQGNSMF
PCCCTKPTDGNCTCIPIPSSWAFAKYLWEWASVRFSWLSL
LVPFVQWFVGLSPTVWLSVIWMMWYWGPSLYNILSPFIPL
LPIFFCLWVYI

L-HBsAg
(SEQ ID NO: 11)
MGGWSAKPRKGMGTNLSVPNPLGFFPDHQLDPAFGANSNN
PDWDFNPNKDHWPEANQVGVGAFGPGFTPPHGGLLGWSSQ
AQGTLHTVPAVPPPASTNRQTGRQPTPISPPLRDSHPQAM
QWNSTAFQQALQDPRVRGLFFPAGGSSSGTVNPAPNIASH
ISSISSRTGDPALNMENITSGFLGPLLVLQAGFFLLTRIL
TIPQSLDSWWTSLNFLGGSPVCLGQNSQSPTSNHSPTSCP
PICPGYRWMCLRRFIIFLFILLLCLIFLLVLLDYQGMLPV
CPLIPGSTTTSTGPCKTCTTPAQGNSMFPSCCCTKPTDGN
CTCIPIPSSWAFAKYLWEWASVRFSWLSLLVPFVQWFVGL
SPTVWLSVIWMMWYWGPSLYNILSPFIPLLPIFFCLWVYI

P03141 Hepatitis B Virus Genotype A2 Subtype Adw2 (Strain Rutter 1979)

PreS1
(SEQ ID NO: 12)
MGGWSSKPRKGMGTNLSVPNPLCFFPDHQLDPAFGANSNNPDWDFNP
VKDDWPAANQVGVGAFGPRLTPPHGGILGWSPQAQGILTTVSTIPPP
ASTNRQSGRQPTPI

PreS2
(SEQ ID NO: 13)
SPPLRDSHPQAMQWNSTAFHQTLQDPRVRGLYLPAGGSSSGTVNPAP
NIASHISS

S-HBsAg
(SEQ ID NO: 14)
ISARTGDPVTNMENITSGFLGPLLVLQAGFFLLTRILTIPQSLDSWW
TSLNFLGGSPVCLGQNSQSPTSNHSPTSCPPICPGYRWMCLRRFIIF
LFILLLCLIFLLVLLDYQGMLPVCPLIPGSTTTSTGPCKTCTTPAQG
NSMFPSCCCTKPTDGNCTCIPIPSSWAFAKYLWEWASVRFSWLSLLV
PFVQWFVGLSPTVWLSAIWMMWYWGPSLYSIVSPFIPLLPIFFCLWV
YI

M-HBsAG
(SEQ ID NO: 15)
SPPLRDSHPQAMQWNSTAFHQTLQDPRVRGLYLPAGGSSSGTVNPAP
NIASHISSISARTGDPVTNMENITSGFLGPLLVLQAGFFLLTRILTI
PQSLDSWWTSLNFLGGSPVCLGQNSQSPTSNHSPTSCPPICPGYRWM
CLRRFIIFLFILLLCLIFLLVLLDYQGMLPVCPLIPGSTTTSTGPCK
TCTTPAQGNSMFPSCCCTKPTDGNCTCIPIPSSWAFAKYLWEWASVR
FSWLSLLVPFVQWFVGLSPTVWLSAIWMMWYWGPSLYSIVSPFIPLL
PIFFCLWVYI

L-HBsAg
(SEQ ID NO: 16)
MGGWSSKPRKGMGTNLSVPNPLGFFPDHQLDPAFGANSNNPDWDFNP
VKDDWPAANQVGVGAFGPRLTPPHGGILGWSPQAGGILTTVSTIPPP
ASTNRQSGRQPTPISPPLRDSHPQAMQWNSTAFHQTLQDPRVRGLYL
PAGGSSSGTVNPAPNIASHISSISARTGDPVTNMENITSGFLGPLLV
LQAGFFLLTRILTIPQSLDSWWTSLNFLGGSPVCLGQNSQSPTSNHS
PTSCPPICPGYRWMCLRRFIIFLFILLLCLIFLLVLLDYQGMLPVCP
LIPGSTTTSTGPCKTCTTPAQGNSMFPSCCCTKPTDGNCTCIPIPSS
WAFAKYLWEWASVRFSWLSLLVPFVQWFVGLSPTVWLSAIWMMWYWG
PSLYSIVSPFIPLLPIFFCLWVYI

Q4R1R8 Hepatitis B Virus Genotype A3 (Isolate Cameroon/CMR711/1994)

PreS1
(SEQ ID NO: 17)
MGGRLPKPRKGMGTNLSVPNPLGFFPDHQLDPAFGANSNNPDWDFNP
IKDHWPQANQVGVGAFGPGFTPPHGGVLGWSPQAGGTLTTVPAVPPP
ASTNRQSGRQPTPI

PreS2
(SEQ ID NO: 18)
SPPLRDSHPQAMQWNSTKFHQTLQDPRVRGLYFPAGGSSSGTVNPAP
NIASHISS

S-HBsAg
(SEQ ID NO: 19)
ISSRIGDPAPTMENITSGFLGPLLVLQAGFFLLTRILTIPQSLDSWW
TSLNFLGEAPVCLGQNSQSPTSNHSPTSCPPICPGYRWMCLRRFIIF
LFILLLCLIFLLVLLDCQGMLPVCPLIPGSTTTSTGPCRTCTTPAQG
NSMFPSCCCTKPTDGNCTCIPIPSSWAFAKYLWEWASVRFSWLSLLV
PFVQWFVGLSPTVWLSVIWMMWYWGPSLYNILSPFIPLLPIFFCLWV
YI

M-HBsAg
(SEQ ID NO: 20)
SPPLRDSHPQAMQWNSTKFHQTLQDPRVRGLYFPAGGSSSGTVNPAP
NIASHISSISSRIGDPAPTMENITSGFLGPLLVLQAGFFLLTRILTI
PQSLDSWWTSLNFLGEAPVCLGQNSQSPTSNHSPTSCPPICPGYRWM
CLRRFIIFLFILLLCLIFLLVLLDCQGMLPVCPLIPGSTTTSTGPCR
TCTTPAQGNSMFPSCCCTKPTDGNCTCIPIPSSWAFAKYLWEWASVR
FSWLSLLVPFVQWFVGLSPTVWLSVIWMMWYWGPSLYNILSPFIPLL
PIFFCLWVYI

L-HBsAg
(SEQ ID NO: 21)
MGGRLPKPRKGMGTNLSVPNPLGFFPDHQLDPAFGANSNNPDWDFNP
IKDHWPQANQVGVGAFGPGFTPPHGGVLGWSPQAGGTLTTVPAVPPP
ASTNRQSGRQPTPISPPLRDSHPQAMQWNSTKFHQTLQDPRVRGLYF
PAGGSSSGTVNPAPNIASHISSISSRIGDPAPTMENITSGFLGPLLV
LQAGFFLLTRILTIPQSLDSWWTSLNFLGEAPVCLGQNSQSPTSNHS
PTSCPPICPGYRWMCLRRFIIFLFILLLCLIFLLVLLDCQGMLPVCP
LIPGSTTTSTGPCRTCTTPAQGNSMFPSCCCTKPTDGNCTCIPIPSS
WAFAKYLWEWASVRFSWLSLLVPFVQWFVGLSPTVWLSVIWMMWYWG
PSLYNILSPFIPLLPIFFCLWVYI

Q8JXB9 Hepatitis B Virus Genotype B1 (Isolate Japan/Ry30/2002)

PreS1
(SEQ ID NO: 22)
MGGWSSKPRKGMGTNLSVPNPLGFEPDHQLDPAFKANSENPDWDLNP
HKDNWPDAHKVGVGAFGPGETPPHGGLLGWSPQAGGILTSVPAAPPP
ASTNRQSGRQPTPL

PreS2
(SEQ ID NO: 23)
SPPLRDTHPQAMQWNSTTFHQTLQDPRVRALYLPAGGSSSGTVSPAQ
NTVSAISS

S-HBsAG
(SEQ ID NO: 24)
ILSTTGDPVPNMENIASGLLGPLLVLQAGFFSLTKILTIPQSLDSWW
TSLSFLGGTPVCLGQNSQSPISSHSPTCCPPICPGYRWMYLRRFIIX
LCILLLCLIFLLVLLDYQGMLPVCPLIPGSSTTSTGPCKTCTTPAQG
TSMFPSCCCTKPTDGNCTCIPIPSSWAFAKYLWEWASVRFSWLSLLV
PFVQWFVGLSPTVWLSVIWMMWYWGPSLYNILSPFMPLLPIFFCLWV
YI

M-HBsAg
(SEQ ID NO: 25)
SPPLRDTHPQAMQWNSTTFHQTLQDPRVRALYLPAGGSSSGTVSPAQ
NTVSAISSILSTTGDPVPNMENIASGLLGPLLVLQAGFFSLTKILTI
PQSLDSWWTSLSFLGGTPVCLGQNSQSPISSHSPTCCPPICPGYRWM
YLRRFIIXLCILLLCLIFLLVLLDYQGMLPVCPLIPGSSTTSTGPCK
TCTTPAQGTSMFPSCCCTKPTDGNCTCIPIPSSWAFAKYLWEWASVR
FSWLSLLVPFVQWFVGLSPTVWLSVIWMMWYWGPSLYNILSPFMPLL
PIFFCLWVYI

L-HBsAg
(SEQ ID NO: 26)
MGGWSSKPRKGMGTNLSVPNPLGFFPDHQLDPAFKANSENPDVJDLN
PHKDNWPDAHKVGVGAFGPGFTPPHGGLLGwSPQAGGILTSVPAAPP
PASTNRQSGRQPTPLSPPLRDTHPQAMQWNSTTFHQTLQDPRVRALY

-continued
LPAGGSSSGTVSPAQNTVSAISSILSTTGDPVPNMENIASGLLGPLL

VLQAGFFSLTKILTIPQSLDSWWTSLSFLGGTPVCLGQNSQSPISSH

SPTCCPPICPGYRWMYLRRFIIXLCILLLCLIFLLVLLDYQGMLPVC

PLIPGSSTTSTGPCKTCTTPAQGTSMFPSCCCTKPTDGNCTCIPIPS

SWAFAKYLWEWASVRFSWLSLLVPFVQWFVGLSPTVWLSVIWMMWYW

GPSLYNILSPFMPLLPIFFCLWVYI

Q9PWW3 Hepatitis B Virus Genotype B2 (Isolate Vietnam/16091//1992)

PreS1
(SEQ ID NO: 27)
MGGWSSKPRKGMGTNLSVPNPLGFFPDHQLDPAFKANSENPDWDLNP

HKDNWPDANKVGVGAFGPGFTPPHGGLLGWSPQAQGLLTTVPAAPPP

ASTNRQSGRQPTPL

PreS2
(SEQ ID NO: 28)
SPPLRDTHPQAMQWNSTTFHQTLQDPRVRALYFPAGGSSSGTVSPAQ

NTVSTISS

S-HBsAg
(SEQ ID NO: 29)
ILSKTGDPVPNMENIASGLLGPLLVLQAGFFLLTKILTIPQSLDSWW

TSLNFLGGTPVCLGQNSQSQISSHSPTCCPPICPGYRWMCLRRFIIF

LCILLLCLIFLLVLLDYQGMLPVCPLIPGSSTTSTGPCKTCTTPAQG

TSMFPSCCCTKPTDGNCTCIPIPSSWAFAKYLWEWASVRFSWLSLLV

PFVQWFVGLSPTVWLSVIWMMWFWGPSLYNILSPFMPLLPIFFCLWV

YI

M-HBsAg
(SEQ ID NO: 30)
SPPLRDTHPQAMQWNSTTFHQTLQDPRVRALYFPAGGSSSGTVSPAQ

NTVSTISSILSKTGDPVPNMENIASGLLGPLLVLQAGFFLLTKILTI

PQSLDSWWTSLNFLGGTPVCLGQNSQSQISSHSPTCCPPICPGYRWM

CLRRFIIFLCILLLCLIFLLVLLDYQGMLPVCPLIPGSSTTSTGPCK

TCTTPAQGTSMFPSCCCTKPTDGNCTCIPIPSSWAFAKYLWEWASVR

FSWLSLLVPFVQWFVGLSPTVWLSVIWMMWFWGPSLYNILSPFMPLL

PIFFCLWVYI

L-HBsAg
(SEQ ID NO: 31)
MGGWSSKPRKGMGTNLSVPNPLGFFPDHQLDPAFKANSENPDWDLNP

HKDNWPDANKVGVGAFGPGFTPPHGGLLGWSPQAQGLLTTVPAAPPP

ASTNRQSGRQPTPLSPPLRDTHPQAMQWNSTTFHQTLQDPRVRALYF

PAGGSSSGTVSPAQNTVSTISSILSKTGDPVPNMENIASGLLGPLLV

LQAGFFLLTKILTIPQSLDSWWTSLNFLGGTPVCLGQNSQSQISSHS

PTCCPPICPGYRWMCLRRFIIFLCILLLCLIFLLVLLDYQGMLPVCP

LIPGSSTTSTGPCKTCTTPAQGTSMFPSCCCTKPTDGNCTCIPIPSS

WAFAKYLWEWASVRFSWLSLLVPFVQWFVGLSPTVWLSVIWMMWFWG

PSLYNILSPFMPLLPIFFCLWVYI

Q76R62 Hepatitis B Virus Genotype C Subtype Ayr (Isolate Human/Japan/Okamoto/-)

PreS1
(SEQ ID NO: 32)
MGGWSSKPRQGMGTNLSVPNPLGFFPDHQLDPAFGANSNNPDWDFNP

NKDHWPEANQVGAGAFGPGFTPPHGGLLGWSPQAQGILTTLPAAPPP

ASTNRQSGRQPTPI

PreS2
(SEQ ID NO: 33)
SPPLRDSHPQAMQWNSTTFHQALLDPRVRGLYFPAGGSSSGTVNPVP

TTASPISS

S-HBsAg
(SEQ ID NO: 34)
IFSRTGDPAPNMESTTSGFLGPLLVLQAGFFLLTRILTIPQSLDSWW

TSLNFLGGAPTCPGQNSQSPTSNHSPTSCPPTCPGYRWMCLRRFIIF

LFILLLCLIFLLVLLDYQGMLPVCPLLPGTSTTSTGPCRTCTIPAQG

TSMFPSCCCTKPSDGNCTCIPIPSSWAFARFLWEWASVRFSWLSLLV

PFVQWFVGLSPTVWLSAIWMMWYWGPSLYNILSPFLPLLPIFFCLWV

YI

M-HBsAg
(SEQ ID NO: 35)
SPPLRDSHPQAMQWNSTTFHQALLDPRVRGLYFPAGGSSSGTVNPVP

TTASPISSIFSRTGDPAPNMESTTSGFLGPLLVLQAGFFLLTRILTI

PQSLDSWWTSLNFLGGAPTCPGQNSQSPTSNHSPTSCPPTCPGYRWM

CLRRFIIFLFILLLCLIFLLVLLDYQGMLPVCPLLPGTSTTSTGPCR

TCTIPAQGTSMFPSCCCTKPSDGNCTCIPIPSSWAFARFLWEWASVR

FSWLSLLVPFVQWFVGLSPTVWLSAIWMMWYWGPSLYNILSPFLPLL

PIFFCLWVYI

L-HBsAg
(SEQ ID NO: 36)
MGGWSSKPRQGMGTNLSVPNPLGFFPDHQLDPAFGANSNNPDWDFNP

NKDHWPEANQVGAGAFGPGFTPPHGGLLGWSPQAQGILTTLPAAPPP

ASTNRQSGRQPTPISPPLRDSHPQAMQWNSTTFHQALLDPRVRGLYF

PAGGSSSGTVNPVPTTASPISSIFSRTGDPAPNMESTTSGFLGPLLV

LQAGFFLLTRILTIPQSLDSWWTSLNFLGGAPTCPGQNSQSPTSNHS

PTSCPPTCPGYRWMCLRRFIIFLFILLLCLIFLLVLLDYQGMLPVCP

LLPGTSTTSTGPCRTCTIPAQGTSMFPSCCCTKPSDGNCTCIPIPSS

WAFARFLWEWASVRFSWLSLLVPFVQWFVGLSPTVWLSAIWMMWYWG

PSLYNILSPFLPLLPIFFCLWVYI

P03138 Hepatitis B Virus Genotype D Subtype Ayw (Isolate France/Tiollais/1979)

PreS1
(SEQ ID NO: 37)
MGQNLSTSNPLGFFPDHQLDPAFRANTANPDWDFNPNKDTWPDANKVG

AGAFGLGFTPPHGGLLGWSPQAQGILQTLPANPPPASTNRQSGRQPTP

L

-continued

PreS2
(SEQ ID NO: 38)
SPPLRNTHPQAMQWNSTTFHQTLQDPRVRGLYFPAGGSSSGTVNPVLT
TASPLSS

S-HBsAg
(SEQ ID NO: 39)
IFSRIGDPALNMENITSGFLGPLLVLQAGFFLLTRILTIPQSLDSWWT
SLNFLGGTTVCLGQNSQSPTSNHSPTSCPPTCPGYRWMCLRRFIIFLF
ILLLCLIFLLVLLDYQGMLPVCPLIPGSSTTSTGPCRTCMTTAQGTSM
YPSCCCTKPSDGNCTCIPIPSSWAFGKFLWEWASARFSWLSLLVPFVQ
WFVGLSPTVWLSVIWMMWYWGPSLYSILSPFLPLLPIFFCLWVYI

M-HBsAg
(SEQ ID NO: 40)
SPPLRNTHPQAMQWNSTTEHQTLQDPRVRGLYEPAGGSSSGTVNPVLT
TASPLSSIFSRIGDPALNMENITSGFLGPLLVLQAGFFLLTRILTIPQ
SLDSWWTSLNFLGGTTVCLGQNSQSPTSNHSPTSCPPTCPGYRWMCLR
RFIIFLFILLLCLIFLLVLLDYQGMLPVCPLIPGSSTTSTGPCRTCMT
TAQGTSMYPSCCCTKPSDGNCTCIPIPSSWAFGKFLWEWASARFSWLS
LLVPFVQWFVGLSPTVWLSVIWMMWYWGPSLYSILSPFLPLLPIFFCL
WVYI

L-HBsAg
(SEQ ID NO: 41)
MGQNLSTSNPLGFFPDHQLDPAFRANTANPDWDFNPNKDTWPDANKVG
AGAFGLGFTPPHGGLLGWSPQAQGILQTLPANPPPASTNRQSGRQPTP
LSPPLRNTHPQAMQWNSTTFHQTLQDPRVRGLYFPAGGSSSGTVNPVL
TTASPLSSIFSRIGDPALNMENITSGFLGPLLVLQAGFFLLTRILTIP
QSLDSWWTSLNELGGTTVCLGQNSQSPTSNHSPTSCPPTCPGYRWMCL
RRFIIFLFILLLCLIFLLVLLDYQGMLPVCPLIPGSSTTSTGPCRTCM
TTAQGTSMYPSCCCTKPSDGNCTCIPIPSSWAFGKFLWEWASARFSWL
SLLVPFVQWFVGLSPTVWLSVIWMMWYWGPSLYSILSPFLPLLPIFFC
LWVYI

Q69603 Hepatitis B Virus Genotype E Subtype Ayw4 (Isolate Kou) GN=S PE=1 SV=2

PreS1
(SEQ ID NO: 42)
MGLSWTVPLEWGKNISTTNPLGFFPDHQLDPAFRANTRNPDWDHNPN
KDHWTEANKVGVGAFGPGFTPPHGGLLGWSPQAQGMLKTLPADPPPA
STNRQSGRQPTPI

PreS2
(SEQ ID NO: 43)
TPPLRDTHPQAMQWNSTTFHQALQDPRVRGLYFPAGGSSSGTVNPVP
TTASLISS

S-HBsAg
(SEQ ID NO: 44)
IFSRIGDPAPNMESITSGFLGPLLVLQAGFFLLTKILTIPQSLDSWW
TSLNFLGGAPVCLGQNSQSPTSNHSPTSCPPICPGYRWMCLRRFIIF
LFILLLCLIFLLVLLDYQGMLPVCPLIPGSSTTSTGPCRTCMTLAQG
TSMFPSCCCSKPSDGNCTCIPIPSSWAFGKFLWEWASARFSWLSLLV
PFVQWFAGLSPTVWLSVIWMMWYWGPSLYDILSPFIPLLPIFFCLWV
YI

M-HBsAg
(SEQ ID NO: 45)
TPPLRDTHPQAMQWNSTTFHQALQDPRVRGLYFPAGGSSSGTVNPVP
TTASLISSIFSRIGDPAPNMESITSGFLGPLLVLQAGFFLLTKILTI
PQSLDSWWTSLNFLGGAPVCLGQNSQSPTSNHSPTSCPPICPGYRWM
CLRRFIIFLFILLLCLIFLLVLLDYQGMLPVCPLIPGSSTTSTGPCR
TCMTLAQGTSMFPSCCCSKPSDGNCTCIPIPSSWAFGKFLWEWASAR
FSWLSLLVPFVQWFAGLSPTVWLSVIWMMWYWGPSLYDILSPFIPLL
PIFFCLWVYI

L-HBsAg
(SEQ ID NO: 46)
MGLSWTVPLEWGKNISTTNPLGFFPDHQLDPAFBANTRNPDWDHNPN
KDHVWTEANKVGVGAFGPGFTPPHGGLLGWSPQAQGMLKTLFADPPP
ASTNRQSGRQPTPITPPLRDTHPQAMQWNSTTFHQALQDPRVRGLYF
PAGGSSSGTVNPVPTTASLISSIFSRIGDPAPNMESITSGFLGPLLV
LQAGFFLLTKILTIPQSLDSWWTSLNFLGGAPVCLGQNSQSPTSNHS
PTSCPPICPGYRWMCLRRFIIFLFILLLCLIFLLVLLDYQGMLPVCP
LIPGSSTTSTGPCRTCMTLAQGTSMFPSCCCSKPSDGNCTCIPIPSS
WAFGKFLWEWASARFSWLSLLVPFVQWFAGLSPTVWLSVIWMMWYWG
PSLYDILSPFIPLLPIFFCLWVYI

Q99HS3 Hepatitis B Virus Genotype F1 (Isolate Argentina/Sa11/2000)

PreS1
(SEQ ID NO: 47)
MGAPLSTTRRGMGQNLSVPNPLGFFPDHQLDPLFRANSSSPDWDFNK
NKDNWPMANKVGVGGYGPGPPHGGLLGWSPQAQGVLTTLPADPPPAS
TNRRSGRKPTPV

PreS2
(SEQ ID NO: 48)
SPPLRDTHPQAMQWNSTQFHQALLDPRVRALYFPAGGSSSETQNPAP
TIASLTSS

S-HBsAg
(SEQ ID NO: 49)
IFLKTGGPATNMDNITSGLLGPLLVLQAVCFLLTKILTIPQSLDSWW
TSLNELGGTPGCPGQNSQSPTSNHLPTSCPPTCPGYRWMCLRRFIIF
LFILLLCLIFLLVLVDYQGMLPVCPPLPGSTTTSTGPCKTCTTLAQG
TSMFPSCCCSKPSDGNCTCIPIPSSWALGKYLWEWASARFSWLSLLV
QFVQWCVGLSPTVWLLVIWMIWYWCPNLCSILSPFIPLLPIFCYLWV
SI

M-HBsAg
(SEQ ID NO: 50)
SPPLRDTHPQAMQWNSTQFHQALLDPRVRALYFPAGGSSSETQNPAP
TIASLTSSIFLKTGGPATNMDNITSGLLGPLLVLQAVCFLLTKILTI

PQSLDSWWTSLNFLGGTPGCPGQNSQSPTSNHLPTSCPPTCPGYRWM
CLRRFIIFLFILLLCLIFLLVLVDYQGMLPVCPPLPGSTTTSTGPCK
TCTTLAQGTSMFPSCCCSKPSDGNCTCIPIPSSWALGKYLWEWASAR
FSWLSLLVQFVQWCVGLSPTVWLLVIWMIWYWGPNLCSILSPFIPLL
PIFCYLWVSI

L-HBsAg
(SEQ ID NO: 51)
MGAPLSTTRRGMGQNLSVPNPLGFFPDHQLDPLFRANSSSPDWDFNK
NKDNWPMANKVGVGGYGPGFTPPHGGLLGWSPQAQGVLTTLPADPPP
ASTNRRSGRKPTPVSPPLRDTHPQAMQWNSTQFHQALLDPRVRALYF
PAGGSSSETQNPAPTIASLTSSIFLKTGGPATNMDNITSGLLGPLLV
LQAVCFLLTKILTIPQSLDSWWTSLNFLGGTPGCPGQNSQSPTSNHL
PTSCPPTCPGYRWMCLRRFIIFLFILLLCLIFLLVLDYQGMLPVCP
PLPGSTTTSTGPCKTCTTLAQGTSMFPSCCCSKPSDGNCTCIPIPSS
WALGKYLWEWASARFSWLSLLVQFVQWCVGLSPTVWLLVIWMIWYWG
PNLCSILSPFIPLLPIFCYLWVSI

Q99HR4 Hepatitis B Virus Genotype F2 (Isolate Argentina/Sa16/2000)

PreS1
(SEQ ID NO: 52)
MGAPLSTTRRGMGQNLSVPNPLGFFPEHQLDPLFRANSSSPDWDFNK
NKDTWPMANKVGVGGYGPGFTPPHGGLLGWSPQAQGVLTTLPADPPP
ASTNRRSGRKPTPV

PreS2
(SEQ ID NO: 53)
SPPLRDTHPQAMQWNSTQFHQALLDPRVRALYFPAGGSSSETQNPAP
TIASLTSS

S-HBsAg
(SEQ ID NO: 54)
IFSKTGGPAMNMDSITSGLLGPLLVLQAVCFLLTKILTIPQSLDSWW
TSLNFLGGLPGCPGQNSQSPTSNHLPTSCPPTCPGYRWMCLRRFIIF
LFILLLCLIFLLVLLDYQGMLPVCPLIPGSTTTSTGPCKTCTTLAQG
TSMFPSCCCSKPSDGNCTCIPIPSSWALGKYLWEWASARFSWLSLLV
QFVQWCVGLSPTVWLLVIWMIWYWGPNLCSILSPFIPLLPIFCYLWV
SI

M-HBsAg
(SEQ ID NO: 55)
SPPLRDTHPQAMQWNSTQFHQALLDPRVRALYFPAGGSSSETQNPAP
TIASLTSSIFSKTGGPAMNMDSITSGLLGPLLVLQAVCFLLTKILTI
PQSLDSWWTSLNFLGGLPGCPGQNSQSPTSNHLPTSCPPTCPGYRWM
CLRRFIIFLFILLLCLIFLLVLLDYQGMLPVCPLIPGSTTTSTGPCK
TCTTLAQGTSMFPSCCCSKPSDGNCTCIPIPSSWALGKYLWEWASAR
FSWLSLLVQFVQWCVGLSPTVWLLVIWMIWYWGPNLCSILSPFIPLL
PIFCYLWVSI

L-HBsAg
(SEQ ID NO: 56)
MGAPLSTTRRGMGQNLSVPNPLGFFPEHQLDPLFRANSSSPDWDFNK
NKDTWPMANKVGVGGYGPGFTPPHGGLLGWSPQAQGVLTTLPADPPP
ASTNRRSGRKPTPVSPPLRDTHPQAMQWNSTQFHQALLDPRVRALYF
PAGGSSSETQNPAPTIASLTSSIFSKTGGPAMNMDSITSGLLGPLLV
LQAVCFLLTKILTIPQSLDSWWTSLNFLGGLPGCPGQNSQSPTSNHL
PTSCPPTCPGYRWMCLRRFIIFLFILLLCLIFLLVLLDYQGMLPVCP
LIPGSTTTSTGPCKTCTTLAQGTSMFPSCCCSKPSDGNCTCIPIPSS
WALGKYLWEWASARFSWLSLLVQFVQWCVGLSPTVWLLVIWMIWYWG
PNLCSILSPFIPLLPIFCYLWVSI

Q9IBI3 Hepatitis B virus genotype G (isolate IG29227/2000)

PreS1
(SEQ ID NO: 57)
MGLSWTVPLEWGKNLSASNPLGFLPDHQLDPAFRANTNNPDWDENPK
KDPWPEANKVGVGAYGPGETPPHGGLLGWSPQSQGTLTTLPADPPPA
STNRQSGRQPTPI

PreS2
(SEQ ID NO: 58)
SPPLRDSHPQAMQWNSTAFHQALQNPKVRGLYFPAGGSSSGIVNPVP
TIASHISS

S-HBsAg
(SEQ ID NO: 59)
IFSRIGDPAPNMENITSGFLGPLLVLQAGFFLLTRILTIPQSLDSWW
TSLNFLGGVPVCPGLNSQSPTSNHSPISCPPTCPGYRWMCLRRFIIF
LFILLLCLIFLLVLLDYQGMLPVCPLIPGSTTTSTGPCKTCTTPAQG
NSMYPSCCCTKPSDGNCTCIPIPSSWAFAKYLWEWASVRFSWLSLLV
PFVQWFVGLSPTVWLSAIWMMWYWGPNLYNILSPFIPLLPIFFCLWV
YI

M-HBsAg
(SEQ ID NO: 60)
SPPLRDSHPQAMQWNSTAFHQALQNPKVRGLYFPAGGSSSGIVNPVP
TIASHISSIFSRIGDPAPNMENITSGFLGPLLVLQAGFFLLTRLTI
PQSLDSWWTSLNFLGGVFVCPGLNSQSPTSNHSPISCPPTCPGYRWM
CLRRFIIFLFILLLCLIFLLVLLDYQGMLPVCPLIPGSTTTSTGPCK
TCTTPAQGNSMYPSCCCTKPSDGNCTCIPIPSSWAFAKYLWEWASVR
FSWLSLLVPFVQWFVGLSPTVWLSAIWMMWYWGPNLYNILSPFIPLL
PIFFCLWVYI

L-HBsAg
(SEQ ID NO: 61)
MGLSWTVPLEWGKNLSASNPLGFLPDHQLDPAFRANTNNPDWDENPK
KDPWPEANKVGVGAYGPGFTPPHGGLLGWSPQSQGTLTTLPADPPPA
STNRQSGRQPTPISPPLRDSHPQAMQWNSTAFHQALQNPKVRGLYFP
AGGSSSGIVNPVPTIASHISSIFSRIGDPAPNMENITSGFLGPLLVL
QAGFFLLTRILTIPQSLDSWWTSLNFLGGVPVCPGLNSQSPTSNHSP

-continued
```
ISCPPTCPGYRWMCLRRFIIFLFILLLCLIFLLVLLDYQGMLPVCPL

IPGSSTTSTGPCKTCTTPAQGNSMYPSCCCTKPSDGNCTCIPIPSSW

AFAKYLWEWASVRFSWLSLLVPFVQWFVGLSPTVWLSAIWMMWYWGP

NLYNILSPFIPLLPIFFCLWVYI
```

Q8JMY6 Hepatitis B Virus Genotype H (Isolate United States/LAS2523/2002)

PreS1
(SEQ ID NO: 62)
```
MGAPLSTARRGMGQNLSVPNPLGFFPDHQLDPLFRANSSSPDWDFNT

NKDNWPMANKVGVGGFGPGFTPPHGGLLGWSPQAQGILTTSPPDPPP

ASTNRRSGRKPTPV
```

PreS2
(SEQ ID NO: 63)
```
SPPLRDTHPQAMQWNSTQFHQALLDPRVRGLYFPAGGSSSETQNPAP

TIASLTSS
```

S-HBsAg
(SEQ ID NO: 64)
```
IFSKTGDPAMNMENITSGLLRPLLVLQAVCFLLTKILTIPQSLDSWW

TSLNFLGVPPGCPGQNSQSPISNHLPTSCPPTCPGYRWMCLRRFIIF

LFILLLCLIFLLVLLDYQGMLPVCPLLPGSTTTSTGPCKTCTTLAQG

TSMFPSCCCTKPSDGNCTCIPIPSSWAFGKYLWEWASARFSWLSLLV

QFVQWCVGLSPTVWLLVIWMIWYWGPNLCSILSPFIPLLPIFCYLWA

SI
```

M-HBsAg
(SEQ ID NO: 65)
```
SPPLRDTHPQAMQWNSTQFHQALLDPRVRGLYFPAGGSSSETQNPAP

TIASLTSSIFSKTGDPAMNMENITSGLLRPLLVLQAVCFLLTKILTI

PQSLDSWWTSLNFLGVPPGCPGQNSQSPISNHLPTSCPPTCPGYRWM

CLRRFIIFLFILLLCLIFLLVLLDYQGMLPVCPLLPGSTTTSTGPCK

TCTTLAQGTSMFPSCCCTKPSDGNCTCIPIPSSWAFGKYLWEWASAR

FSWLSLLVQFVQWCVGLSPTVWLLVIWMIWYWGPNLCSILSPFIPLL

PIFCYLWASI
```

L-HBsAg
(SEQ ID NO: 66)
```
MGAPLSTARRGMGQNLSVPNPLGFFPDHQLDPLFRANSSSPDWDFNT

NKDNWPMANKVGVGGFGPGFTPPHGGLLGWSPQAQGILTTSPPDPPP

ASTNRRSGRKPTPVSPPLRDTHPQAMQWNSTQFHQALLDPRVRGLYF

PAGGSSSETQNPAPTIASLTSSIFSKTGDPAMNMENITSGLLRPLLV

LQAVCFLLTKILTIPQSLDSWWTSLNFLGVPPGCPGQNSQSPISNHL

PTSCPPTCPGYRWMCLRRFIIFLFILLLCLIFLLVLLDYQGMLPVCP

LLPGSTTTSTGPCKTCTTLAQGTSMFPSCCCTKPSDGNCTCIPIPSS

WAFGKYLWEWASARFSWLSLLVQFVQWCVGLSPTVWLLVIWMIWYWG

PNLCSILSPFIPLLPIFCYLWASI
```

In various further embodiments, the composition may comprise an HBVpreS1/ S2Ag or S-HBsAg polypeptide at least 91%, 92%, 93%, 94%, 95%, 96%, 97%, 98%, 99%, or 100% identical over the length of the amino acid sequence of the sequences shown above. In various embodiments, additional HBVpreS1/ S2Ag mutations may be included (alone or in combination). These mutations may include, but are not limited to, the preS1 S98T substitution (PLOS One 9: e110012, 2014), the preS1 F53L substitution (J Med Virol 85: 1698, 2013), or the preS1 A39R and preS1 S96A/T substitutions (Clin Microbial Infect 18: E412, 2012).

In all of these embodiments, the composition may further comprise an amino acid linker position between the CD180 binding ligand and the HBVpreS1/ S2Ag or S-HBsAg. The linker may be of any suitable length and amino acid composition, depending on the intended use. In one embodiment, the linker is between about 2-40 amino acids in length. In other embodiments, the linker may be between 10-30 or 15-25 amino acids in length. In another embodiment, the linker may be a linker rich in glycine and serine residues. In one specific embodiment, the linker may comprise the amino acid sequence (SEQ ID NO: 69)

GGGGSGGGGSGGGGSGGGGS.

In various further embodiments, the composition may comprise or consist of a polypeptide at least 90% identical over its length to the following amino acid sequence of G28-8LH-scAb-PreS1-S2-His protein (expressed)

(SEQ ID NO: 67)

(METPAQLLFL LLLWLPDTTG) DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG GGGSGGGGSG GGGSGGGGST GEVQLQQSGP ELVKPGASMK ISCKASGYSF

181 TGYTMNWVKQ SHGKTLEWIG LINPYNGVTS YNQKFKDKAT LTVDKSSSTA YMELLSLTSE

241 DSAIYYCARD YNYDYFDYWG QGTTLTVSSD LEPKSSDKTH TCPPCPAPEL LGGSSVFLFP

301 PKPKDTLMIS RTPEVTCVVV DVSHEDPEVK FNWYVDGVEV HNAKTKPREE QYNSTYRVVS

361 VLTVLHQDWL NGKEYKCSVS NKALPASIEK TISKAKGQPR EPQVYTLPPS REEMTKNQVS

421 LTCLVKGFYP SDIAVEWESN GQPENNYKTT PPVLDSDGSF FLYSKLTVDK SRWQQGNVFS

481 CSVMHEALHN HYTQKSLSLS PGKGGGGSGG GGSGGGGSGG GGSMGGWSSK PRQGMGTNLS

541 VPNPLGFFPD HQLDPAFGAN SNNPDWDFNP VNKDHWPEANQ GAGAFGPGF TPPHGGLLGW

-continued

```
601 SPQAQGILTT LPAAPPPAST NRQSGRQPTP ISPPLRDSHP QAMQWNSTTF HQALLDPRVR

661 GLYFPAGGSS SGTVNPVPTT ASPISSIFSR TGDPAPN (HHH HHH)
Amino acids 1-20: Leader (optional)
Amino acids 21-129: G28-8VL (Bold)
Amino acids 130-149: Gly-Ser Linker
Amino acids 150-269: G28-8VH (Bold and underlined)
Amino acids 270-503: Hing-CH2-CH3
Amino acids 504-533: Gly-Ser Linker
Amino acids 534-597: preS1/preS2
Amino acids 698-703: 6xHis
Residues in parentheses are optional
```

The compositions of any embodiment or combination of embodiments of the disclosure may be provided as a stand-alone composition, or may be provided as part of a molecular scaffold. In various embodiments, the composition may be attached to molecular scaffold. Any suitable scaffold can be used, including but not limited to a VNAR single domain antibody (shark variable new antigen receptor), a lamprey variable lymphocyte receptor, a Im 7(colicin immunity 7 protein), an anticalin (lipocalin transport proteins), an FN3 (fibronectin 3) monobody, a DARPin (designed ankyrin repeat proteins), an affibody (Z domain of protein A), a single domain antibody, e.g, isolated from camelids or antibody libraries, and aptamer, etc., with CD180-binding polypeptide loops.

In another embodiment, the composition of any embodiment or combination of embodiments of the disclosure further comprises an adjuvant. While adjuvant is not required to induce rapid activation of HBVpreS1/ S2Ag or S-HBsAg, addition of adjuvant to the compositions can result in additional enhancement of the immune response when the compositions are used in the methods of the disclosure. Any suitable adjuvant can be used, including but not limited to inorganic compounds (aluminum hydroxide, aluminum phosphate, calcium phosphate hydroxide, beryllium, etc.), mineral oil, detergents, cytokines, toll-like receptor agonists, Freund's complete adjuvant, Freund's incomplete adjuvant, squalene, etc. In a preferred embodiment, the adjuvant comprises or consists of a toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and a-tocopherol, squalene and polysorbate 80 in an oil-in-water emulsion. The adjuvant may be present in the composition as an unlinked component or a linked component, depending on the adjuvant used.

In another embodiment, the compositions of the disclosure can be modified to extend half-life, such as by attaching at least one molecule to the composition for extending serum half-life, including but not limited to a polyethylene glycol (PEG) group, serum albumin, a serum albumin binding domain, transferrin, transferrin receptor or the transferrin-binding portion thereof, or combinations thereof. As used herein, the word "attached" refers to a covalently or non-covalently conjugated substance. The conjugation may be by genetic engineering or by chemical means.

The compositions of the present disclosure may be stored in any suitable buffer.

In a second aspect, the present disclosure provides isolated nucleic acids encoding the composition of any embodiment of the first aspect of the disclosure. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. In one non-limiting embodiment, the isolated nucleic acids encode a polypeptide of the disclosure noted herein. In other embodiments, the isolated nucleic acids comprise or consist of the nucleotide sequence shown below.

```
G28-8LH-scAb-PreS1-S2-His 2142 bp
                                                    (SEQ ID NO: 68)
  1 GCGAAGCTTT GAGCCACCAT GGAAACCCCA GCGCAGCTTC TCTTCCTCCT GCTACTCTGG

61 CTCCCAGATA CCACCGGTGA CATCCAGATG ACTCAGTCTC CAGCCTCCCT ATCTGCATCT

121 GTGGGAGAAA CTGTCACCAT CACATGTCGA GCAAGTGAGA AGATTTACAG TTATTTAGCA

181 TGGTATCAGC AGAAACAGGG AAAATCTCCT CAGCTCCTGG TCTATAACGC AAAAACCTTA

241 GCAGAAGGTG TGCCATCAAG GTTCAGTGTC AGTGGATCAG GCACACAGTT TTCTCTGAGG

301 ATCAACAGCC TGCAGCCTGA AGATTTTGGG ACTTATTACT GTCAACATCA TTTTGGTTCT

561 CCTCGGACGT TCGGTGGAGG CACCAAACTG GAAATCAAAG ATCTCGGAGG AGGTGGCTCA

421 GGTGGTGGAG GATCTGGAGG AGGTGGGAGT GGTGGAGGTG GTTCTACCGG TGAGGTCCAG

481 CTGCAACAGT CTGGACCTGA ACTGGTGAAG CCTGGAGCTT CAATGAAGAT ATCCTGCAAG

541 GCTTCTGGTT ACTCATTCAC TGGCTACACC ATGAACTGGG TGAAGCAGAG CCATGGAAAG

601 ACCCTTGAAT GGATTGGACT TATTAATCCT TACAATGGTG TTACTAGCTA CAACCAGAAG

661 TTCAAGGACA AGGCCACATT AACTGTAGAC AAGTCATCCA GCACAGCCTA CATGGAACTC
```

-continued

```
 721 CTCAGTCTGA CATCTGAGGA CTCTGCAATC TATTACTGTG CAAGAGACTA TAATTACGAC

781 TACTTTGACT ACTGGGGCCA AGGCACCACT CTCACAGTCT CCTCAGATCT CGAGCCCAAA

841 TCTTCTGACA AAACTCACAC ATGTCCACCG TGTCCAGCAC CTGAACTCCT GGGTGGATCG

901 TCAGTCTTCC TCTTCCCCCC AAAACCCAAG GACACTCTCA TGATCTCCCG GACCCCTGAG

961 GTCACGTGCG TGGTGGTGGA CGTGAGCCAC GAAGACLCCG AGGTCAAGTT CAACTGGTAC

1021 GTGGACGGCG TGGAGGTGCA TAATGCCAAG ACAAAGCCAC GGGAGGAGCA GTACAACAGC

1081 ACGTACCGTG TGGTCAGCGT CCTCACCGTC TTGCACCAGG ACTGGCTGAA CGGCAAGGAG

1141 TACAAGTGCT CGGTCTCCAA CAAAGCCCTC CCAGCCTCCA TCGAGAAAAC AATCTCCAAA

1201 GCCAAAGGGC AGCCCCGAGA ACCACAGGTG TACACCCTGC CCCCATCCCG GGAGGAGATG

1261 ACCAAGAACC AGGTCAGCCT GACCTGCCTG GTCAAAGGCT TCTATCCCAG CGACATCGCC

1321 GTGGAGTGGG AGAGCAATGG GCAGCCGGAG AACAACTACA AGACCACGCC TCCCGTGCTG

1381 GACTCCGACG GCTCCTTCTT CCTCTACAGC AAGCTCACCG TGGACAAGAG CAGGTGGCAG

1441 CAGGGGAACG TCTTCTCATG CTCCGTGATG CATGAGGCTC TGCACAACCA CTACACGCAG

1501 AAJAGCCTCT CTCTGTCTCC GGGTAAAGGA GGAGGTGGCT CAGGTGGTGG AGGATCTGGA

1561 GGAGGTGGGA GTGGTGGAGG TGGTTCTATG GGAGGTTGGT CTTCCAAACC TCGACAAGGC

1621 ATGGGGACGA ATCTTTCTGT TCCCAATCCT CTGGGATTCT TTCCCGATCA CCAGTTGGAC

1681 CCTGCGTTCG GAGCCAACTC AAACAATCCA GATTGGGACT TCAACCCCAA CAAGGATCAC

1741 TGGCCAGAGG CAAATCAGGT AGGAGCGGGA GCATTTGGTC CAGGGTTCAC CCCACCACAC

1801 GGAGGCCTTT TGGGGTGGAG CCCTCAGGCT CAGGGCATAT TGACAACACT GCCAGCAGCA

1861 CCTCCTCCTG CCTCCACCAA TCGGCAGTCA GGAAGACAGC CTACTCCCAT CTCTCCACCT

1921 CTAAGAGACA GTCATCCTCA GGCCATGCAG TGGAACTCCA CAACATTCCA CCAAGCTCTG

1981 CTAGATCCCA GAGTGAGGGG CCTATATTTT CCTGCTGGTG GCTCCAGTTC CGGAACAGTA

2041 AACCCTGTTC CGACTACTGC CTCACCCATA TCGTCAATCT TCTCGAGGAC TGGGGACCCT

2101 GCACCGAACC ACCACCATCA TCATCATTGA TAAGGATCCG CG
```

5' end HindIII and 3' end BamHI sites for directional cloning into appropriate expression vector Kozak consensus, GCCACC, right before 5' ATG start codon One 5' in frame stop codon after 5' end HindIII site Two in frame stop codons before 3' end BamHI site In a third aspect, the present disclosure provides nucleic acid vectors comprising the isolated nucleic acid of the second aspect of the disclosure. "Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In a preferred embodiment, the expression vector comprises a plasmid. However, the disclosure is intended to include other expression vectors that serve equivalent functions, such as viral vectors.

The nucleic acids and vectors of the disclosure can be used not only for production of large quantities of the compositions of the disclosure, but also for use as a nucleic acid (such as a DNA) vaccine administered by gene gun or other methods.

In a fourth aspect, the present disclosure provides recombinant host cells comprising the nucleic acid vector of the third aspect of the disclosure. The host cells can be either prokaryotic or eukaryotic. The cells can be transiently or stably transfected. Such transfection of expression vectors into prokaryotic and eukaryotic cells (including but not limited to Chinese hamster ovary (CHO) cells) can be accomplished via any suitable means, including but not limited to bacterial transformations, calcium phosphate co-precipitation, electroporation, or liposome mediated-, DEAE dextran mediated-, polycationic mediated-, or viral mediated transfection.

The recombinant host cells can be used, for example in methods for producing antibody (when the binding protein is an antibody), comprising:

(a) culturing the recombinant host cell of the disclosure under conditions suitable for expression of the nucleic-acid encoded antibody composition; and (b) isolating the antibody composition from the cultured cells.

Suitable conditions for expression of the nucleic-acid encoded antibody composition can be determined by those of skill in the art based on the teachings herein and the specific host cells and vectors used.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein.

In a fifth aspect, the present disclosure provides pharmaceutical compositions, comprising:
    (a) the composition, isolated nucleic acid, or recombinant expression vector of any embodiment or combination of embodiments disclosed herein; and
    (b) a pharmaceutically acceptable carrier.

In this embodiment, the compositions of the disclosure are present in a pharmaceutical formulation. In this embodiment, the compositions are combined with a pharmaceutically acceptable carrier. Suitable acids which are capable of forming such salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The pharmaceutical composition may comprise in addition to the composition of the disclosure (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, leenzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions of the disclosure may be made up in any suitable formulation, preferably in formulations suitable for administration by injection. Such pharmaceutical compositions can be used, for example, in methods of use as vaccines, prophylactics, or therapeutics.

The pharmaceutical compositions may contain any other components as deemed appropriate for a given use, such as additional therapeutics or vaccine components. In one embodiment, the pharmaceutical compositions further comprise toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion.

In a sixth aspect, the present disclosure provides methods for treating or limiting development of an HBV infection or a hepatitis-B virus (HBV)-related disorder, comprising administering to an individual in need thereof an amount effective to treat or limit development of the disorder of the composition, isolated nucleic acid, recombinant expression vector, or pharmaceutical composition, or a pharmaceutical salt thereof, of any embodiment or combination of embodiments of the present disclosure. In one embodiment, the compositions are used prophylactically as vaccines to limit development of HBV infection disease/severity of infectious disease, such as in individuals that have not been exposed to an infectious agent but are at risk of such exposure. In other embodiments, the methods can be used therapeutically to treat people exposed to or chronically infected with HBV.

The methods of the disclosure target antigen to CD180, a surface protein expressed on B cells, macrophages, and dendritic cells, that to produce antigen-specific IgG in the absence of T cell costimulation (such as CD40 deficiency) or the complete absence of T cells (such as TCR β/δ deficiency). Thus, the methods can be used in any therapeutic or prophylactic treatment for HBV infection or vaccination. This approach also finds use, for example, for neonates, the elderly, the immunocompromised, and the immunodeficient, both in specifically targeting cellular populations enriched in underdeveloped or otherwise deficient immune systems and by improving responses to antigens that require linked recognition (carbohydrate epitopes, etc.).

As used herein, "treat" or "treating" means accomplishing one or more of the following in an individual that already has a disorder or has already been exposed to a disorder-causing substance/pathogen: (a) reducing the severity of the disorder; (b) limiting or preventing development of symptoms characteristic of the disorder(s) being treated (ex: immune deficiencies in cancer patients or other patients) undergoing chemotherapy and/or radiation therapy); (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "limiting" or "limiting development of" means accomplishing one or more of the following in an individual that does not have the disorder to be limited: (a) preventing the disorder; (b) reducing the severity of the disorder; and (c) limiting or preventing development of symptoms characteristic of the disorder.

As used herein, an "amount effective" refers to an amount of the composition that is effective for treating and/or limiting the relevant disorder.

While the methods of the disclosure do not require use of an adjuvant, the methods may further comprise administering an adjuvant for possible additional enhancement of the immune response Any suitable adjuvant can be used, including but not limited to toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and a-tocopherol, squalene and polysorbate 80 in an oil-in-water emulsion.

The individual may be any suitable individual, including but not limited to mammals. Preferably the individual is a human. In one embodiment, the individual has a T-cell deficiency and/or a defect in co-stimulation between B cells and T cells, or is immuno-compromised by chronic infections or from acute or chronic taking of immunosuppressive drugs for treatment of autoimmune diseases, or other inflammatory disease . In another embodiment, the individual is less than one month old or is elderly (i.e.: at least 65 years old).

In various other embodiments, the individual has a hepatitis B-related disease, such as hepatitis, hepatitis-related disease, fulminant hepatitis, cirrhosis, and/or hepatocellular carcinoma, and the methods are used to treat the a hepatitis B-related disease, such as hepatitis, hepatitis-related disease, fulminant hepatitis, cirrhosis, and/or hepatocellular carcinoma.

EXAMPLE 1

Generation and Characterization of G28-8LH-scAb-PreS1-S2-his Recombinant Protein Molecules.

```
G28-8LH-scAb-PreS1-S2-His_protein_(expressed)
                                                      (SEQ ID NO: 67)
   1 (METPAQLLFL LLLWLPDTTG) DIQMTQSPAS LSASVGETVT ITCRASEKIY SYLAWYQQKQ

61 GKSPQLLVYN AKTLAEGVPS RFSVSGSGTQ FSLRINSLQP EDFGTYYCQH HFGSPRTFGG

121 GTKLEIKDLG GGGSGGGGSG GGGSGGGGST GEVQLQQSGP ELVKPGASMK ISCKASGYSF

181 TGYTMNWVKQ SHGKTLEWIG LINPYNGVTS YNQKFKDKAT LTVDKSSSTA YMELLSLTSE

241 DSAIYYCARD YNYDYFDYWG QGTTLTVSSD LEPKSSDKTH TCPPCPAPEL LGGSSVFLFP

301 PKPKDTLMIS RTPEVTCVVV DVSHEDPEVK FNWYVDGVEV HNAKTKPREE QYNSTYRVVS

361 VLTVLHQDWL NGKEYKCSVS NKALPASIEK TISKAKGQPR EPQVYTLPPS REEMTKNQVS

421 LTCLVKGFYP SDIAVEWESN GQPENNYKTT PPVLDSDGSF FLYSKLTVDK SRWQQGNVFS

481 CSVMHEALHN HYTQKSLSLS PGKGGGGSGG GGSGGGGSGG GGSMGGWSSK PRQGMGTNLS

541 VPNPLGFFPD HQLDPAFGAN SNNPDWDFNP NKDHWPEANQ VGAGAFGPGE TPPHGGLLGW

601 SPQAQGILTT LPAAPPPAST NRQSGRQPTP ISPPLRDSHP QAMQWNSTTE HQALLDPRVR

661 GLYFPAGGSS SGTVNPVPTT ASPISSIFSR TGDPAPN(HHH HHH)
Amino acids 1-20: Leader (optional)
Amino acids 21-129: G28-8VL (Bold)
Amino acids 130-149: Gly-Ser Linker
Amino acids 150-269: G28-8VH (Bold and underlined)
Amino acids 270-503: Hing-CH2-CH3
Amino acids 504-533: Gly-Ser Linker
Amino acids 534-697: preS1/preS2
Amino acids 698-703: 6xHis
Residues in parentheses are optional
```

G28-8 (anti-human CD180)-scAb-PreS1/ S2 recombinant protein molecules. The inventors have demonstrated that for the specific anti-CD180 antibody, G28-8, a single chain antibody (scAb) in the form of VLVH-human IgG1 Fc retains both the efficient binding as well as the biological properties of its parent G28-8 IgG. The G28-8LH scAb is used to create G28-8LH-scAb-PreS1-S2-His recombinant protein constructs. It is anticipated that scFv generated from other anti-CD180 antibodies may retain the antibody characteristics in either the VLVH, VHVL, or only the VHVL configuration.

Production of recombinant the G28-8LH-scAb-PreS1-S2-His protein. Complementary DNAs (cDNAs) encoding the G28-8LH-scAb-PreS1-S2-His recombinant proteins (FIG. 1, G28-8LH-scAb-PreS1-S2-His protein) were cloned into the mammalian expression vector pTT5 that harbors a CMV promoter to drive protein expression. Transient transfection of these plasmids into Chinese hamster ovary (CHO) cells was done using Lipofectamine™ reagents (Invitrogen Carlsbad, CA) or polyethyleninmine (PEI). Small-scale transfection optimization using 5%, 20% and 80% ratios of expression plasmid in the lipofection reagent was conducted to identify to optimal plasmid to lipofection reagent ratios for larger scale expression. Once optimized transfection conditions are established, a large-scale transfection will be conducted for each of the plasmids for recombinant protein production. Nickel affinity chromatography, e.g., using the HisPurNi-NTA$^{Tm}$ resin (Thermo Fisher Scientific Inc., Rockford Ill.), was used to purify the recombinant proteins. The cDNA sequences for the G28-8LH-scAb-HBV-PreS1/S2 protein predicts a polypeptide size of ~75 kDa. The expressed dimeric form of the recombinant protein is predicted to have a molecular weight of 150 kDa.

Figure 2:
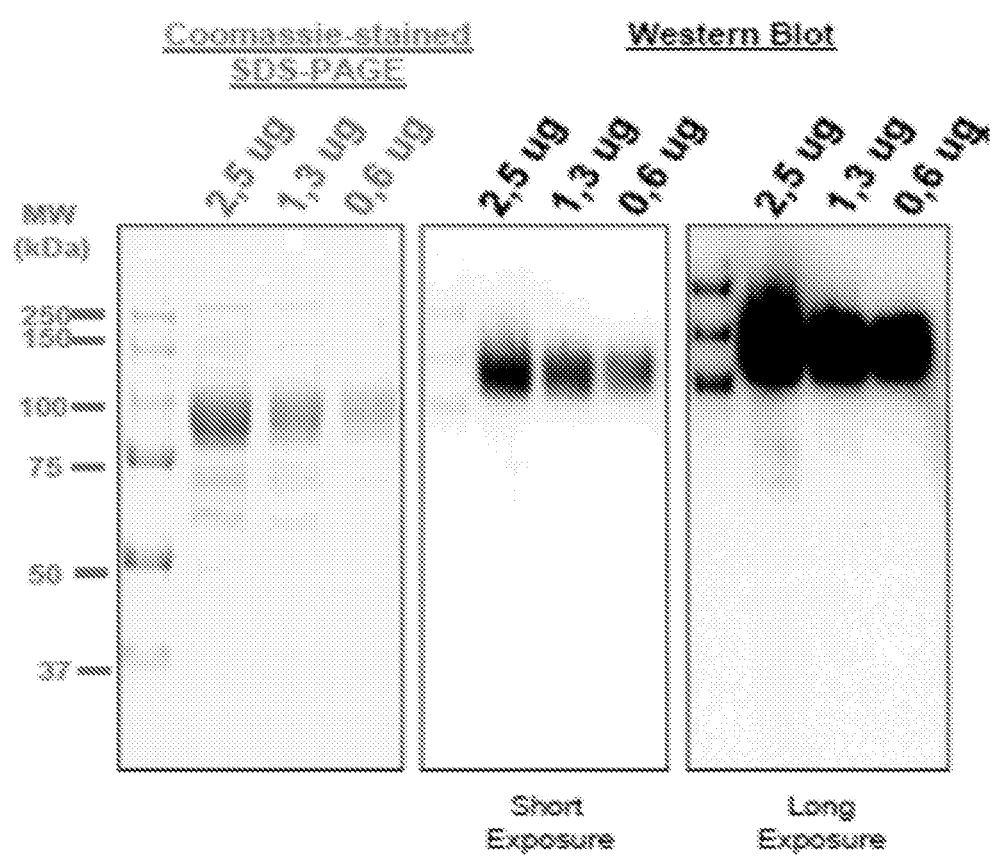
FIG. 2. Characterization of recombinant G28-8LH-scAb-PreS1-S2-His. G28-8LH-scAb-PreS1-S2-His was transiently expressed in CHO cells. Culture supernatant was passed over a Ni2+ affinity chromatography column. Bound G28-8LH-scAb-PreS1-S2-His was eluted with imidazole. Eluted protein (E) was characterized by reducing SDS-PAGE and western blotting using an anti-6x-His antibody.

FIG. 2 shows the results from a 2-liter expression run. The plasmid encoding the G28-8LH-scAb-PreS1-S2-His protein was transiently expressed in CHO cells for 8 days. Culture supernatants (~2 liters) were collected and cellular debris was removed by centrifugation. Clarified culture supernatants were then loaded on to a column containing HisPurNi-NTA™ resin. After washing the column with the wash buffer (50 mM phosphate buffer, pH 7.0, 300 mM NaCl, 1 mM imidazole), bound recombinant protein was eluted with the elution buffer (50 mM phosphate buffer, pH 7.0, 300 mM NaCl, 150 mM imidazole). Protein containing fractions as monitored by absorbance at 280 nM were collected, pooled, and dialyzed against phosphate-buffer saline at pH 7.0. Purified G28-8LH-scAb-PreS1-S2-His and unbound flow through materials from HisPurNi-NTA™ chromatography was analyzed on SDS-PAGE (4-15% gradient under reducing conditions) stained with Coomassie blue. FIG. 2, left panel shows a major protein band migrating at the MW of ~85 kDa, suggesting that G28-8LH-scAb-PreS1-S2-His protein was in fact expressed by CHO cells as an intact protein and secreted into the culture supernatants. A duplicate gel was then transferred onto a nylon membrane and immuno-blotted with an anti-6×-His antibody. Intense anti-6× His signals were only observed at ~85 kDa (FIG. 2, right panel), at the identical MW G28-8LH-scAb-PreS1-S2-His migrated to on the Coomassie blue stained gel (FIG. 2, left panel).

EXAMPLE 2

Characterization of G28-8LH-scAb-PreS1-S2-His

Figure 3:
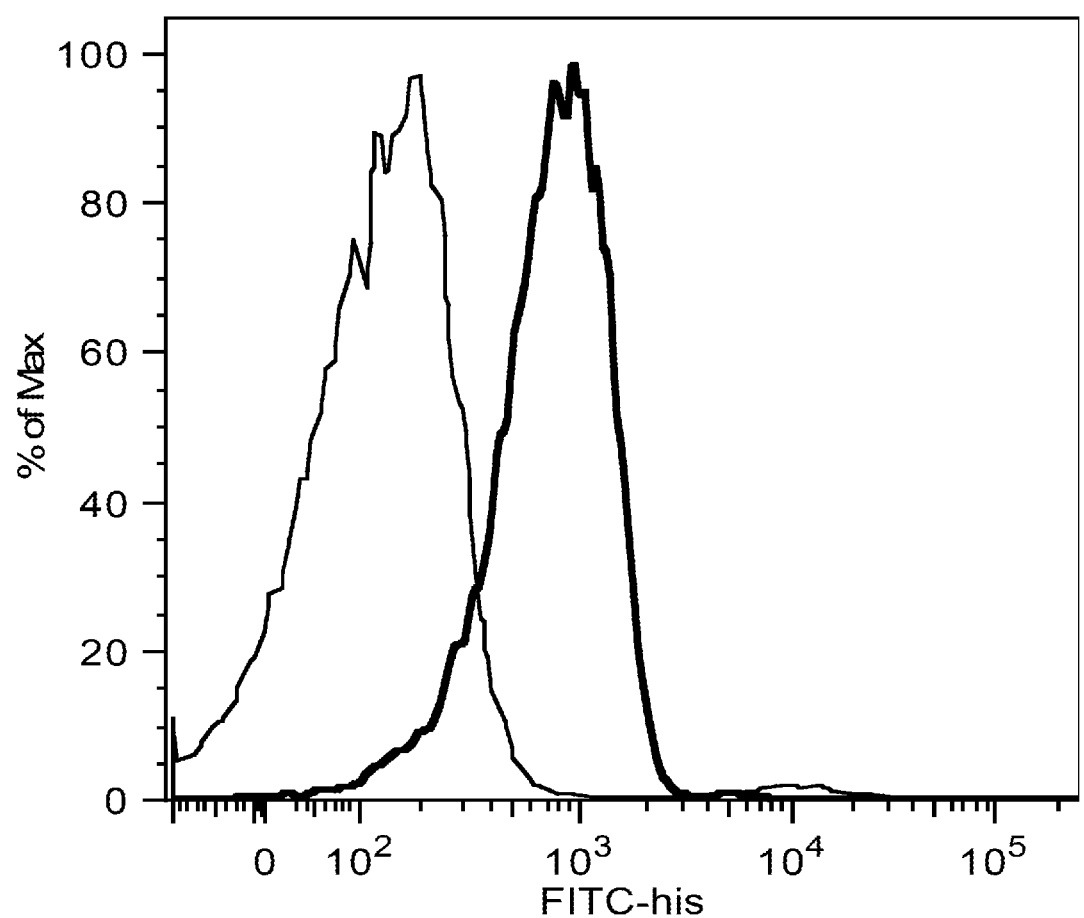
FIG. 3. Binding of recombinant G28-8LH-scAb-PreS1-S2-His to human B cells. Direct binding to human gated CD20+ tonsillar B cells using a FITC-anti-His monoclonal antibody (bold black line). Second step only (light black line).

FIG. 3 shows that human CD20+ tonsillar B cells ($10^6$) were incubated in 96 well round bottom plates with PBSA (PBS w/0.2% BSA+0.2% NaN3) media only (gray) or with the His tagged recombinant protein containing the light and heavy chains of G28-8 anti-human CD180 (LH) G28-8LH-scAb-PreS1-S2-His (black), at 10 μg/ml. After a 40 min incubation on ice, the cells were washed twice (centrifuged at 1200 rpm, 4 min). Then 100 μl of PBSA+5 μl a fluorescein (FITC)-conjugated anti 6× His (FITC-6×-His epitope tag ThermoScientific MA1-81891) were added to the wells, and after a 40 min incubation on ice, cells were washed twice and the level of fluorescence measured by flow cytometry shown on abscissa (log scale). Unstained cells are shown in black. The recombinant protein bound to B cells as shown by binding being above the FITC control, demonstrating binding to CD180 expressed on B cells.

Figure 4:
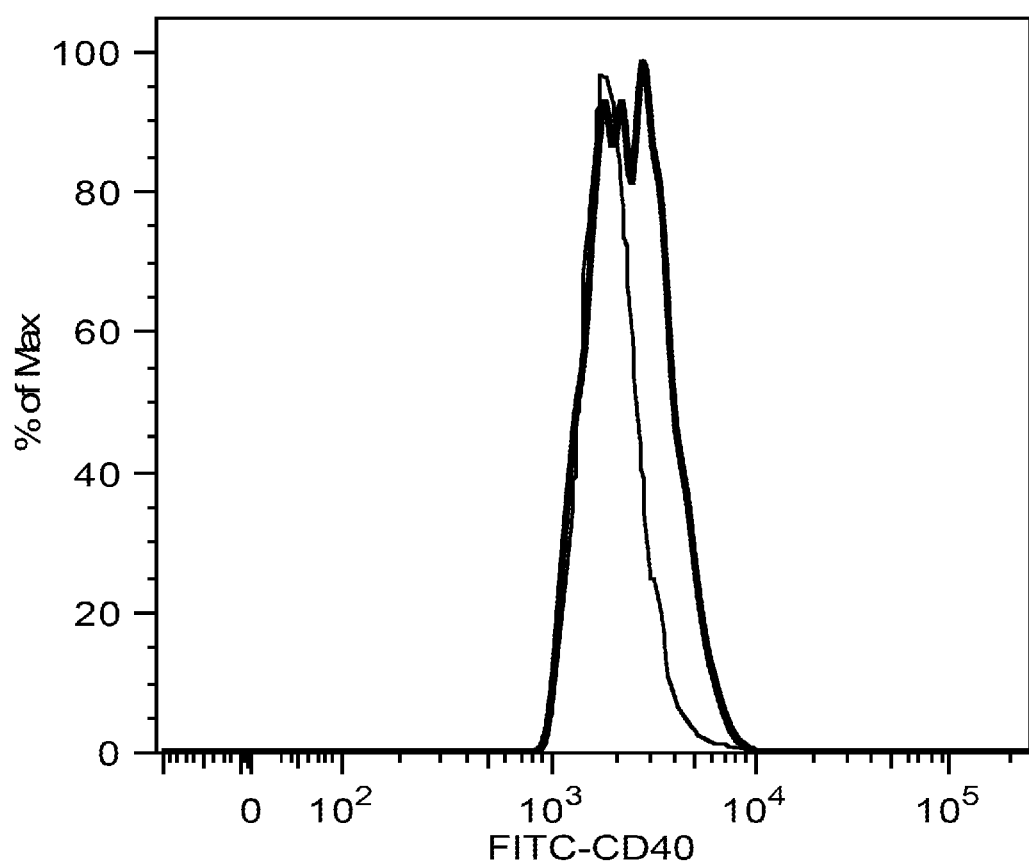
FIG. 4. Recombinant G28-8LH-scAb-PreS1-S2-His activates human B cells. Sheep erythrocyte-binding negative blood mononuclear cells enriched for B cells were incubated at 37 C for 24 hours either with media only (light black line), or with G28-8LH-scAb-PreS1-S2-His (bold black line). Samples were gated for CD20+ cells (Pacific blue-anti-CD20) and levels of CD40 expression measured as an indication of activation using flow cytometry. Graph shows CD40 expression of gated CD20$^+$ B cells.

Ligation of CD180 on B cells has been shown to upregulate CD40 expression[51]. The ability of G28-8LH-scAb-PreS1-S2-His to upregulate CD40 expression was then tested to evaluate its functional activity (FIG. 4). Er-blood mononuclear cells enriched for B cells were incubated for 24 hrs at 37 C with either media (gray line) or 10 μg/ml of G28-8LH-scAb-HBV-PreS1/ S2-His (black line). Samples were washed twice with PBSA, stained with mAb specific for CD20 (Pacific Blue Biolegend™) and CD40 (FITC BD BioSciences) and evaluated for CD40 and CD20 expression using flow cytometry. Graph shows CD40 expression of gated CD20$^+$ B cells. G28-8LH-scAb-PreS1-S2-His upregulated CD40 expression, confirming that G28-8LH-scAb-PreS1-S2-His was functionally active (FIG. 4).

EXAMPLE 3

Figure 5:
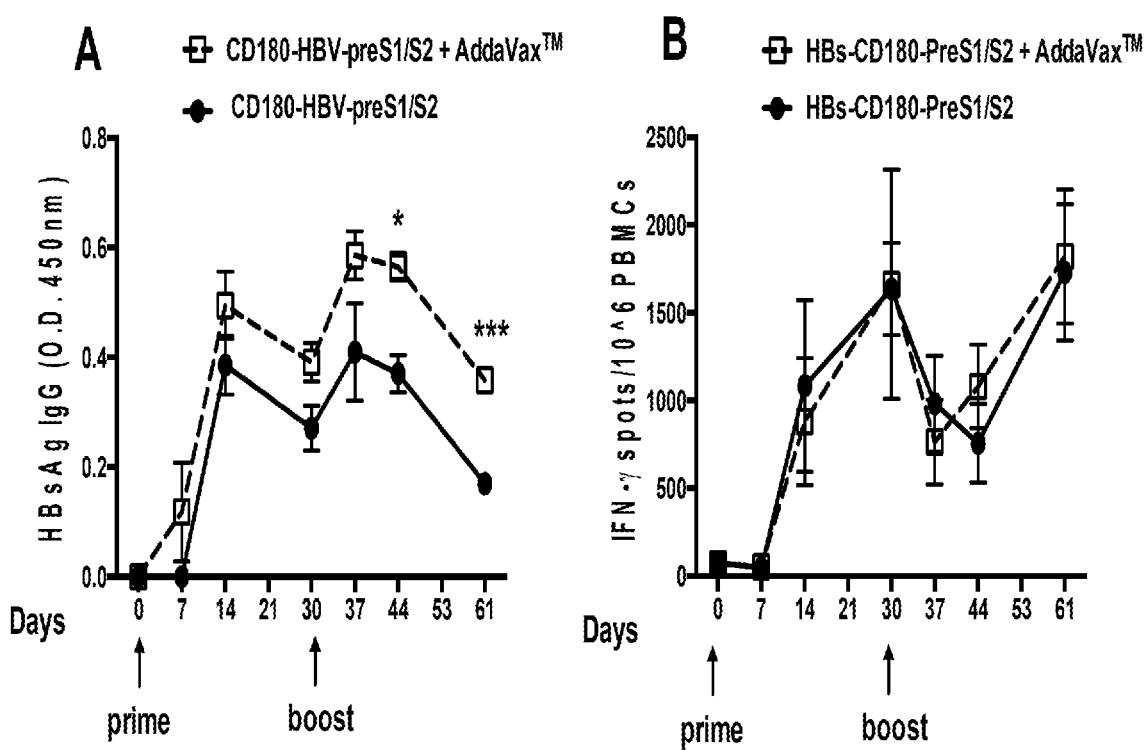
FIG. 5. Immune responses in macaques immunized and boosted with recombinant G28-8LH-scAb-PreS1-S2-His recombinant protein (CD180-HBV-preS1/ S2). Groups of cynomolgus macaques (*Macaca fascicularis*) (N=3) were vaccinated subcutaneously with either: 1) 300 µg of G28-8LH-scAb-PreS1-S2-His (CD180-HBV-PreS1/ S2, black circles); or 2) 300 µg of G28-8LH-scAb-PreS1-S2-His (αCD180-HBV-preS1/S2) plus 0.5 ml Addavax™ (open squares). Animals were vaccinated on days 0 and 30, and serum and heparinized blood samples were obtained on days 0, 7, 14, 30 after primary immunization and days 7, 14, and 30 after secondary immunization. (A) HBV-PreS1-specific IgG antibody levels detected using ELISA. Mean optical densities (O.D.) at each time point±SEM are indicated. (B) HBsAg-specific IFN-γ-producing T cells detected by ELIspot assays. Statistical comparisons between the two groups for each assay were assessed at each timepoint using unpaired t test on samples with equal standard deviation. Significant differences are indicated: *P=0.01, ***P=0.006. For all other timepoints, there was no significant difference in mean responses between the groups.

Induction in Macaques of preS1-S2-Specific IgG Antibody Responses by G28-8LH-scAb-PreS1-S2-His Recombinant Protein The ability of G28-8LH-scAb-PreS1-S2-His to induce humoral and cellular immune responses was examined in a vaccination experiment in cynomolgus macaques (Macaca fascicularis). Groups of macaques (N=3) were vaccinated subcutaneously with either: 1) 300 pg of G28-8LH-scAb-PreS1-S2-His (αCD180-HBV-PreS1/ S2) in 1 ml; or 2) 300 μg of G28-8LH-scAb-PreS1-S2-His co-formulated with 100 μg of the commercial adjuvant AddaVax™ (InVivoGen, San Diego, CA) in a total of 1 ml. Animals were vaccinated on days 0 and 30 and serum and heparinized blood samples were obtained on days 0, 7, 14, 30 (time-points after first dose), 37, 44 and 60 (time-points after second dose). Serum samples were assessed for IgG antibody responses to HBV preS1 by ELISA as follows: a) coating 96 well plates with 200 ng/well purified recombinant preS1 peptide (115 amino acids, Cosmo Bio. Japan cat #BCL-AGS1-01); b) adding serial dilutions of serum samples (100 μl diluted in TBS+ 0.05% tween-20) starting with a 1:1000 dilution, followed by washing and adding HRP-anti-macaque IgG second step (Rockland, 1:5000 dilution). Both groups produced IgG after immunizations (FIG. 5A). The antibody titers increased after each boost. The group receiving recombinant protein with AddaVax™ adjuvant had higher IgG antibody responses compared to group not given AddaVax™ at two time points after the second immunization.

EXAMPLE 4

Induction in macaques of HBV-specific T cell responses by G28-8LH-scAb-PreS1-S2-His To determine the frequency of HBV-PreS1/ S2-specific, intracellular cytokine-producing T cells after vaccination of the macaques, peripheral blood mononuclear cells (PBMCs) were isolated from heparinized blood samples obtained from immunized macaques at the times before and after immunization as noted in Example 3. PBMCs were separated using gradient centrifugation and stimulated in vitro for 18 hours with HBsAg peptide pools (15mers overlapping by 11 amino acids). HBs-specific T cells secreting IFN-γ were detected using paired anti-macaque IFN-γ monoclonal antibodies (U-cytech-BV). Spot forming cells (SFC) were enumerated using an Immunospot™ Analyzer with CTL Immunospot™ Profession Software (Cellular Technology Ltd.). Results shown in FIG. 5B are mean SFC per 1 million PBMC time point±SEM. Tests were run in replicate wells. Net responses shown were determined by subtracting the number of spots from DMSO stimulated control wells from the same animal. Statistical comparisons between the two groups for each assay were assessed at each time point using unpaired t test on samples with equal standard deviation and resuspended in growth media at defined concentrations (~1.2 million cells/condition). The number of HBsAg-specific IFN-γ-producing T cells increased within 14 days after primary immunization with G28-8LH-scAb-PreS1-S2-His only and the addition of the AddaVax™ adjuvant did not increase HBsAg-specific T cell levels.

EXAMPLE 5

Figure 6:
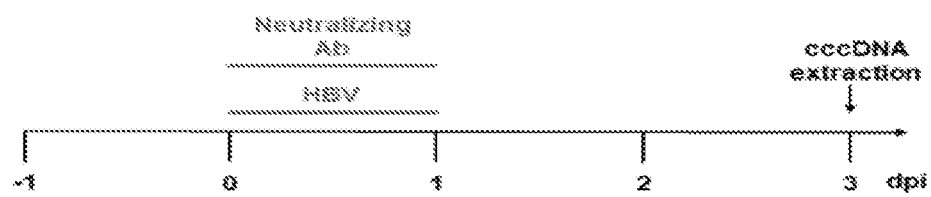
FIG. 6. G28-8LH-scAb-PreS1-S2-His recombinant protein vaccine induced neutralizing antibodies (Abs) that block the production of HBV cccDNA in HBV infected liver cells. Cynomolgus macaques (*Macaca fascicularis*, N=3/ group) received a priming and booster as described in FIG. 11 with either 300 ug G28-8LH-scAb-PreS1-S2-His (A57, A59 and A60) or 300 µg G28-8LH-scAb-PreS1-S2-His co-formulated with 100 µg of the commercial adjuvant, AddaVax™ (A55, A58 and A68, indicated by * in figure). Sera obtained 2 weeks after the second immunization were evaluated for neutralizing antibody activity. (A) The scheme illustrates the treatment schedule with HBV inoculum ($10^3$ Geq per cell) and serum samples (Neutralizing Ab). HepG2-hNTCP cells were treated with pre-bleed serum at a 1:1000 dilution (D) or immune sera from macaques at !:300, 1:1000 or 1:3000 dilution for 16 hours after the time of the HBV inoculation. At 1 day post infection (dpi), the mediums containing 2.5% DMSO were replaced. The cccDNAs were extracted at 3 dpi, and analyzed by real-time PCR. (B) HepG2-hNTCP cells infected with HBV ($10^3$ Geq/cell) were treated with sera as indicated (1:300 D=dilution of the original serum stock to 1/300 as vol/vol, 1:1000 D=dilution of the original serum stock to 1/1000 as vol/vol, 1:3000 D=dilution of the original serum stock to 1/3000 as vol/vol). Pre-bleed serums (1/1000 dilution (vol/vol)) were included as a control. At 3 dpi, cccDNAs were analyzed by real-time PCR. Following digestion of T5 exonuclease, cccDNA was specifically quantified using specific primers. cccDNA was normalized as a ratio to mitochondrial DNA. Representative data are shown with quantification (means ±standard deviation) (n=2).
Figure 6:
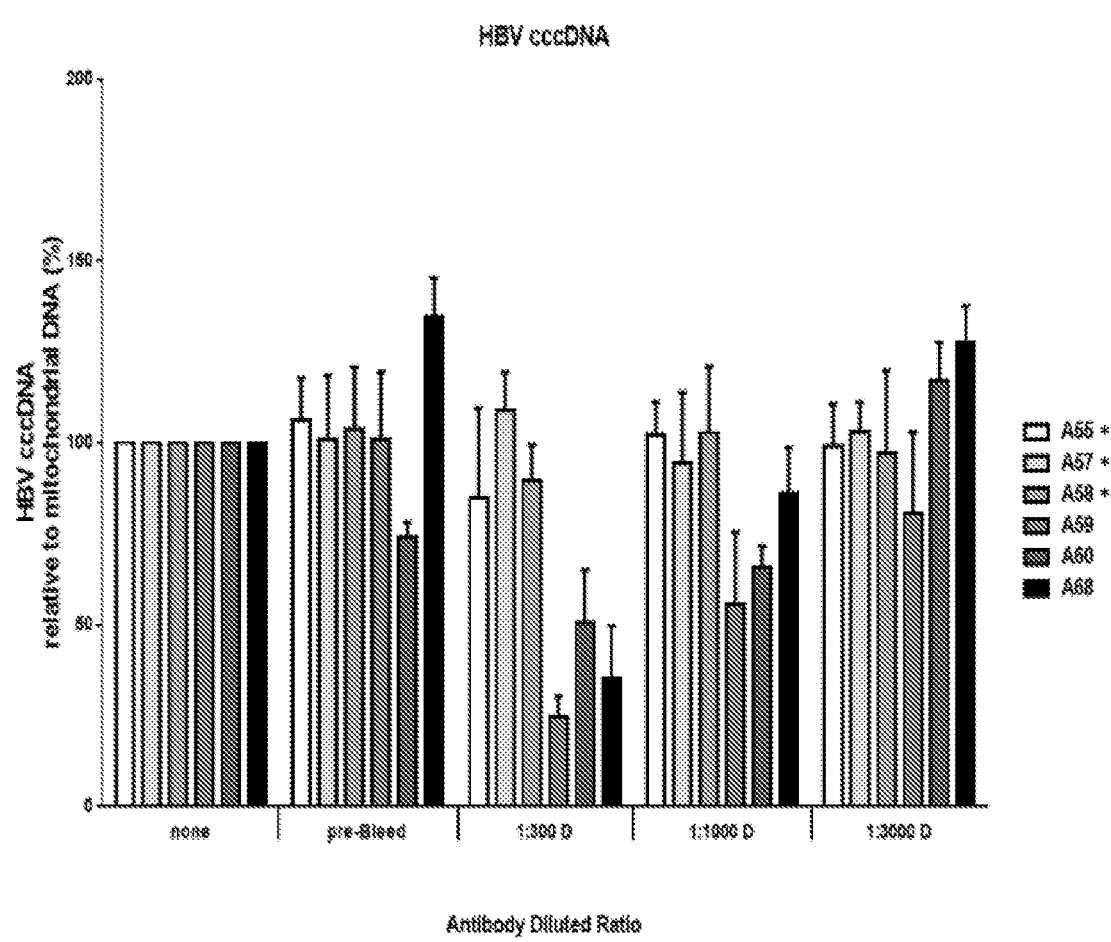

Induction in Macaques of HBV-Specific Neutralizing Antibodies (Abs) by G28-8LH-scAb-PreS1-S2-His To determine the frequency neutralizing antibodies (Abs) to HBV after vaccination of the macaques, sera were from macaques before (pre-bleed) and 14 days after the second immunization as noted in Example 3. HBV particles were obtained from the culture supernatants of HepAD38 cells as an HBV-productive cell line. For HBV infection, HepG2 liver cells expressing the NTCP receptor for HBV (HepG2-hNTCP cells) were seeded in 60-mm dishes or 6-well plates coated with collagen type 1. After one day, cells were inoculated with HBV virions at $10^3$ genome equivalents (Geq) per cell in completed DMEM containing 4% polyethylene glycol (PEG) 8000 for 16h. Then, cells were maintained in completed DMEM containing 2.5% DMSO for additional days. For the virus neutralizing experiment, the sera being tested for neutralizing Abs were added during the inoculation (16 h) as indicated in FIG. 6A.

For analysis of HBV cccDNAs, viral cccDNAs were isolated with the Hirt Extraction Method, for protein-free DNA extraction from HBV-infected cells. Briefly, cells from 60-mm dishes were lysed in 1 ml of lysis buffer containing 50 mM Tris-HCl (pH 7.4), 150 mM NaCl, 10 mM EDTA, and 1% SDS. After 1 h of incubation at room temperature, the lysates were transferred into a 2-ml tube, and this step was followed by the addition of 0.25 ml of 2.5 M KCl, then incubation at 4° C. overnight. The lysates were clarified by centrifugation and extracted with phenol-chloroform. DNA was precipitated with isopropanol overnight and dissolved in Nuclease-free water. The extracted DNA was treated with Plasmid-Safe ATP-dependent Dnase for southern blot analysis or T5 exonuclease for real-time PCR. For real-time PCR, total DNAs were purified from infected cells using DNeasy™ Blood & Tissue Kit (Qiagen). cccDNA levels were expressed as a normalized ratio to mitochondrial DNA, and cccDNA were detected using specific PCR primers.

The sera tested for neutralizing Ab activity included the pre-bleed controls (1:1000 dilution) for each animal and sera obtained from immunized macaques day 14 after a second immunization. The immune sera were tested for neutralizing Ab activity at either a 1:300 dilution (D), a 1:1000 D or a 1:3000 D. Three sera from immunized macaques (day 14 boost) had neutralizing Ab activity that prevented HBV from expressing cccDNA in hepatocytes in vitro, two animals from group 1, and one from group 2 (FIG. 6B). Group 1: G28-8LH-scAb-PreS1-S2-His (300 ug) Monkey ID: A16157, A16159, A16160. Group 2: G28-8LH-scAb-PreS1-S2-His (300 ug)+AddaVax (100 µg) Monkey ID: A16155, A16158, A16168

LITERATURE

1. Bertoletti A, Ferrari C. Adaptive immunity in HBV infection. J Hepatol. 2016. 64: S71-83.
2. Chappell C P, Giltiay N V, Dresch C, Clark E A. Controlling immune responses by targeting antigens to dendritic cell subsets and B cells. Int Immunol. 2014. 26:3-11.
3. Kim H. N., et al., Hepatitis B vaccination in HIV-infected adults: current evidence, recommendations and practical considerations. International journal of STD & AIDS, 2009. 20:595-600.
4. Kubba, A. K., et al., Non-responders to hepatitis B vaccination: a review. Communicable disease and public health/PHLS, 2003. 6:106-12.
5. Ott, J. J., et al., Global epidemiology of hepatitis B virus infection: new estimates of age-specific HBcAg seroprevalence and endemicity. Vaccine 2012. 30:2212-9.
6. Weinbaum C M, Williams I, Mast E E, et al. Recommendations for identification and public health management of persons with chronic hepatitis B virus infection. Centers for Disease Control and Prevention (CDC). MMWR Recomm Rep. 2008. 57(RR-8):1-20.
7. Wasley A, Kruszon-Moran D, Kuhnert W, et al. The prevalence of hepatitis B virus infection in the United States in the era of vaccination. J Infect Dis. 2010. 202:192-201.
8. Mitchell T, Armstrong G L, Hu D J, Wasley A, Painter J A. The increasing burden of imported chronic hepatitis B-United States, 1974-2008. PLoS One. 2011. 6: e27717.
9. Hepatitis B vaccines. Releve epidemiologique hebdomadaire/Section d'hygiene du Secretariat de la Societe des Nations=Weekly epidemiological record/Health Section of the Secretariat of the League of Nations, 2004. 79:255-63.
10. Perz J F et al., The contributions of hepatitis B virus and hepatitis C virus infections to cirrhosis and primary liver cancer worldwide. J Hepatol 2006. 45:529-38.
11. Lavanchy, D., Hepatitis B virus epidemiology, disease burden, treatment, and current and emerging prevention and control measures. J Viral Hep 2004. 11:97-107.
12. Kim W R, Epidemiology of hepatitis B in the United States. Hepatology, 2009. 49: S28-34.
13. Wang L, Zou Z Q, Liu C X, Liu X Z. Immunotherapeutic interventions in chronic hepatitis B virus infection: a review. J Immunol Methods. 2014 May; 407:1-8.
14. Thai H, Campo D S, Lara J, et al. Convergence and coevolution of hepatitis B virus drug resistance. Nat Commun. 2012. 3:789.
15. Menendez-Arias L, Alvarez M, Pacheco B. Nucleoside/nucleotide analog inhibitors of hepatitis B virus polymerase: mechanism of action and resistance. Curr Opin Virol. 2014. 8C:1-9.
16. Wiegand J, van Bornmel F, Berg T, Management of chronic hepatitis B: status and challenges beyond treatment guidelines. Semin Liver Dis 2010; 30:361-377.
17. Luckhaupt S E, Calvert G M. Deaths due to bloodborne infections and their sequelae among health-care workers. Am J Ind Med. 2008. 51:812-24.
18. Beck, J. and M. Nassal, Hepatitis B virus replication. World J Gastroenterol WJG, 2007. 13:48-64.
19. Bruss V. Hepatitis B virus morphogenesis. World J Gastroenterol. 2007. 13:65-73.
20. Gerlich W H. Prophylactic vaccination against hepatitis B: achievements, challenges and perspectives. Med Microbiol Immunol. 2015. 204:39-55.
21. Eng N F, Bhardwaj N, Mulligan R, Diaz-Mitoma F. The potential of 1018 ISS adjuvant in hepatitis B vaccines: HEPLISAV™. Hum Vaccin Immunother. 2013. 9:1661-72.
22. Jilg W. Novel hepatitis B vaccines. Vaccine. 1998. 16 Suppl:S65-8.
23. Madalinski K, Sylvan S P, Hellstrom U, Mikolajewicz J, Zembrzuska-Sadkowska E, Piontek E. Antibody 23. responses to preS components after immunization of children with low doses of BioHepB. Vaccine. 2001 Oct. 12; 20(1-2):92-7.
24. Rendi-Wagner P, Shouval D, Genton B, et al. Comparative immunogenicity of a PreS/S hepatitis B vaccine in non- and low responders to conventional vaccine. Vaccine. 2006. 24:2781-9.
25. Ni Y, Lempp F A, Mehrle S, et al. Hepatitis B and D viruses exploit sodium taurocholate co-transporting polypeptide for species-specific entry into hepatocytes. Gastroenterology. 2014 April; 146(4):1070-83.
26. Li W. NTCP is receptor for HBV The hepatitis B virus receptor. Annu Rev Cell Dev Biol. 2015; 31:125-47.
27. Chi S W, Kim J. Yi G S, Hong H J, Ryu S E. Broadly neutralizing anti-HBV antibody binds to non-epitope regions of preS1. FEBS Lett. 2009. 583:3095-100.
28. Ferrari C, Penna A, Bertoletti A et al. The preS1 antigen of hepatitis B virus is highly immunogenic at the T cell level in man. J Clin Invest. 1989. 84:1314-9.
29. Krawczyk A, Ludwig C, Jochum C et al. Induction of a robust T- and B-cell immune response in non- and low-responders to conventional vaccination against hepatitis B by using a third generation PreS/S vaccine. Vaccine. 2014. 32:5077-82.
30. Dion S, Bourgine M, Godon O, Levillayer F, Michel M L. Adeno-associated virus-mediated gene transfer leads to persistent hepatitis B virus replication in mice expressing HLA-A2 and HLA-DR1 molecules. J Virol. 2013 May; 87(10):5554-63.
31. Bian Y, Zhang Z, Sun Z et al. Vaccines Targeting PreS1 Domain Overcome Immune Tolerance in HBV Carrier Mice. Hepatology. 2017 Apr. 26. doi: 10.1002/hep.29239. [Epub ahead of print]
32. Valentine M A, Clark E A, Shu G L, Norris N A, Ledbetter J A. Antibody to a novel 95-kDa surface glycoprotein on human B cells induces calcium mobilization and B cell activation. J Immunol. 1988. 140:4071-8.
34. Miyake, K., et al., Murine B cell proliferation and protection from apoptosis with an antibody against a 105-kD molecule: unresponsiveness of X-linked immunodeficient B cells. J Exp Med 1994. 180:1217-24.
34. Miyake, K., et al., RP105, a novel B cell surface molecule implicated in B cell activation, is a member of the leucine-rich repeat protein family. J Immunol 1995. 154:3333-40.
35. Alving C R, Peachman K K, Rao M, Reed S G. Adjuvants for human vaccines. Curr Opin Immunol. 2012. 24:310-5.
36. Shimazu, R., et al., MD-2, a molecule that confers lipopolysaccharide responsiveness on Toll-like receptor 4. J Exp Med 1999. 189:1777-82.
37. Hebeis, B., et al., Vav proteins are required for B-lymphocyte responses to LPS. Blood, 2005. 106:635-40.
38. Hebeis, B. J., et al., Activation of virus-specific memory B cells in the absence of T cell help. J Exp Med 2004. 199:593-602.
39. Yazawa, N., et al., CD19 regulates innate immunity by the toll-like receptor RP105 signaling in B lymphocytes. Blood, 2003. 102:1374-80.
40. Chaplin, J. W., et al., Anti-CD180 (RP105) activates B cells to rapidly produce polyclonal Ig via a T cell and MyD88-independent pathway. J Immunol, 2011. 187: 4199-209.
41. Schultz T E, Blumenthal A. The RP105/ MD-1 complex: molecular signaling mechanisms and pathophysiological implications. J Leukoc Biol. 2017 January; 101(1):183-192.
42. Ohto U, Miyake K, Shimizu T. Crystal structures of mouse and human RP105/ MD-1 complexes reveal unique dimer organization of the toll-like receptor family. J Mol Biol. 2011 Nov. 4; 413(4):815-25.
43. Yoon S I, Hong M, Wilson I A. An unusual dimeric structure and assembly for TLR4 regulator RP105-MD-1. Nat Struct Mol Biol. 2011 Aug. 21; 18(9):1028-35.
45. Chaplin J W, Chappell C P, Clark E A. Targeting antigens to CD180 rapidly induces antigen-specific IgG, affinity maturation and immunologic memory. 2013. J Exp Med 210:2135-46.
46. Ramos, H. J. and M. Gale, Jr., RIG-I like receptors and their signaling crosstalk in the regulation of antiviral immunity. Curr Opin Virol, 2011. 1:67-76.
47. Maxon E R, Siegrist C A. The next decade of vaccines: societal and scientific challenges. Lancet. 2011. 378:348-59.
48. Liang Y et al., Predictors of relapse in chronic hepatitis B after discontinuation of anti-viral therapy. Aliment Pharmacol Ther, 2011. 34:344-52.
49. Suthar M S, Diamond M S, Gale M, Jr. West Nile virus infection and immunity. 2013. Nat Rev Microbiol 11:115-128.
50. Coffman R L, Sher A, Seder R A. Vaccine adjuvants: putting innate immunity to work. Immunity. 2010. 33:492-503.
51. Clark E A, Shu G L, Lüscher B, Draves K E, Banchereau J, Ledbetter J A, Valentine M A. Activation of human B cells. Comparison of the signal transduced by IL-4 to four different competence signals. J Immunol. 1989. 143: 3873-80.

Loudon P T, Yager E J, Lynch D T, Narendran A, Stagnar C, Franchini A M, Fuller J T, White P A, Nyuandi J, Wiley C A, Murphey-Corb M, Fuller D H. GM-CSF increases mucosal and systemic immunogenicity of an H1N1 influenza DNA vaccine administered into the epidermis of non-human primates. PLoS One. 2010. 5: e11021.

Toita R, Kawano T, Kang J H, Murata M. Applications of human hepatitis B virus preS domain in bio- and nano-technology. World J Gastroenterol. 2015 Jun. 28; 21(24): 7400-11.

Chen Y, Bai Y, Guo X, Wang W, et al. Selection of affinity-improved neutralizing human scFv against HBV PreS1 from CDR3 VH/VL mutant library. Biologicals. 2016 July; 44(4):271-5.

We claim:

1. A nucleic acid encoding a polypeptide comprising an amino acid sequence at least 90% identical to the amino acid sequence of SEQ ID NO:67 residues 21-697.

2. The nucleic acid of claim 1, wherein the encoded polypeptide comprises an amino acid sequence having at least 95% identity to the amino acid sequence of SEQ ID NO:67 residues 21-697.

3. The nucleic acid of claim 1, wherein the encoded polypeptide comprises an amino acid sequence having at least 98% identity to the amino acid sequence of SEQ ID NO:67 residues 21-697.

4. The nucleic acid of claim 1, wherein the encoded polypeptide comprises the amino acid sequence of SEQ ID NO:67 residues 21-697.

5. The nucleic acid of claim 1, wherein the encoded polypeptide comprises an amino acid sequence having at least 90% identity to the amino acid sequence of SEQ ID NO:67.

6. The nucleic acid of claim 1, wherein the encoded polypeptide comprises an amino acid sequence having at least 95% identity to the amino acid sequence of SEQ ID NO:67.

7. The nucleic acid of claim 1, wherein the encoded polypeptide comprises an amino acid sequence having at least 98% identity to the amino acid sequence of SEQ ID NO:67.

8. The nucleic acid of claim 1, wherein the encoded polypeptide comprises the amino acid sequence of SEQ ID NO:67.

9. The nucleic acid of claim 1, wherein the nucleic acid is RNA.

10. The nucleic acid of claim 2, wherein the nucleic acid is RNA.

11. The nucleic acid of claim 4, wherein the nucleic acid is RNA.

12. The nucleic acid of claim 8, wherein the nucleic acid is RNA.

13. An expression vector comprising the isolated nucleic acid of claim 1 operatively linked to a promoter.

14. An expression vector comprising the isolated nucleic acid of claim 4 operatively linked to a promoter.

15. A pharmaceutical composition, comprising
    (a) the nucleic acid claim 1; and
    (b) a pharmaceutically acceptable carrier.

16. A pharmaceutical composition, comprising
    (a) the nucleic acid claim 4; and
    (b) a pharmaceutically acceptable carrier.

17. A pharmaceutical composition, comprising
    (a) the nucleic acid claim 8; and
    (b) a pharmaceutically acceptable carrier.

18. A pharmaceutical composition, comprising
    (a) the nucleic acid claim 9; and
    (b) a pharmaceutically acceptable carrier.

19. A pharmaceutical composition, comprising
    (a) the nucleic acid claim 11; and
    (b) a pharmaceutically acceptable carrier.

20. A pharmaceutical composition, comprising
    (a) the nucleic acid claim 12; and
    (b) a pharmaceutically acceptable carrier.

* * * * *